US00RE40911E

(19) United States
(12) Reissued Patent
MacLeod

(10) Patent Number: US RE40,911 E
(45) **Date of Reissued Patent: *Sep. 8, 2009**

(54) CANINE ERYTHROPOIETIN GENE AND RECOMBINANT PROTEIN

(75) Inventor: James N. MacLeod, Versailles, KY (US)

(73) Assignee: Cornell Research Foundation, Inc., Ithaca, NY (US)

( * ) Notice: This patent is subject to a terminal disclaimer.

(21) Appl. No.: 11/239,627

(22) PCT Filed: Apr. 21, 1999

(86) PCT No.: PCT/US99/08705

§ 371 (c)(1),
(2), (4) Date: Dec. 11, 2000

(87) PCT Pub. No.: WO99/54486

PCT Pub. Date: Oct. 28, 1999

Related U.S. Patent Documents

Reissue of:
(64) Patent No.: 6,696,411
Issued: Feb. 24, 2004
Appl. No.: 09/673,429
Filed: Dec. 11, 2000

U.S. Applications:
(60) Provisional application No. 60/082,669, filed on Apr. 22, 1998.

(51) Int. Cl.

| | |
|---|---|
| ***A61K 38/00*** | (2006.01) |
| ***C12N 15/00*** | (2006.01) |
| ***C12N 5/00*** | (2006.01) |
| ***C07K 14/00*** | (2006.01) |
| ***C07K 14/505*** | (2006.01) |

(52) U.S. Cl. ..... 514/2; 435/69.1; 435/325; 435/320.1; 530/397; 530/399

(58) Field of Classification Search ..... None
See application file for complete search history.

(56) References Cited

U.S. PATENT DOCUMENTS

| | | | |
|---|---|---|---|
| 3,865,801 | A | 2/1975 | Chiba et al. |
| 4,558,006 | A | 12/1985 | Egrie |
| 4,677,195 | A | 6/1987 | Hewick et al. |
| 4,703,008 | A | 10/1987 | Lin |
| 4,732,889 | A | 3/1988 | Cynshi et al. |
| 4,835,260 | A | 5/1989 | Shoemaker |
| 5,089,397 | A | 2/1992 | Kushner et al. |
| 5,219,739 | A | 6/1993 | Tischer et al. |
| 5,354,934 | A | 10/1994 | Pitt et al. |
| 5,441,868 | A | 8/1995 | Lin |
| 5,457,089 | A | 10/1995 | Fibi et al. |
| 5,547,933 | A | 8/1996 | Lin |
| 5,595,900 | A | 1/1997 | Lowe |
| 5,597,562 | A | 1/1997 | Nomura et al. |
| 5,621,080 | A | 4/1997 | Lin |
| 5,661,125 | A | 8/1997 | Strickland |
| 5,756,349 | A | 5/1998 | Lin |
| 5,856,298 | A | 1/1999 | Strickland |
| 5,955,422 | A | 9/1999 | Lin |

FOREIGN PATENT DOCUMENTS

| | | | |
|---|---|---|---|
| EP | 409-133 | A | 1/1991 |
| EP | 1-013-288 | A | 6/2000 |
| WO | WO 91/05867 | | 5/1991 |
| WO | WO 94/02611 | | 2/1994 |

OTHER PUBLICATIONS

Wells, Additivity of Mutational Effects in Proteins. Biochemistry. vol. 29, No. 37 pp. 8509–8517 (Sep. 1990).*

Wen et al., "Erythropoietin Structure–Function Relationships: High Degree of Sequence Homology Among Mammals," *Blood*82(5):1507–1516 (1993).

Macleod et al., "Expression and Bioactivity of Recombinant Canine Erythropoietin, "*Am. J. Vet. Res.*59(9):1144–1148 (1998).

Cowgill et al., "Use of Recombinant Human Erythropoietin for Management of Anemia in Dogs and Cats with Renal Failure," *J. Am. Vet. Med. Assoc.*212(4):521–528 (1998).

Spivak, "Recombinant Human Erythropoietin and the Anemia of Cancer," *Blood* 84(4):997–1004 (1994).

Randolph et al., "Comparison of the Biological Activity and Safety of Recombinant Canine Erythropoietin to Recombinant Human Erythropoietin in Normal Beagle Dogs," American College of Veterinary Internal Medicine, Official Abstract Form for Oral and Poster Presentations, 16$^{th}$ Annual Veterinary Medical Forum (May 1998) (abstract).

Randolph et al., "Comparison of Biological Activity and Safety of Recombinant Canine Erythropoietin with that of Recombinant Human Erythropoietin in Clinically Normal Dogs, " *Am. J. Vet. Res.*60(5):636–642 (1999).

* cited by examiner

*Primary Examiner*—Marianne P Allen
*Assistant Examiner*—Regina M DeBerry
(74) *Attorney, Agent, or Firm*—Nixon Peabody LLP

(57) ABSTRACT

One aspect of the present invention is an isolated nucleic acid molecule encoding canine erythropoietin. The present invention also relates to an isolated canine erythropoietin protein or polypeptide. Another aspect of the present invention is a method for providing erythropoietin therapy to a dog or a cat including administering recombinant canine erythropoietin to a dog or a cat in need of erythropoietin therapy is an amount sufficient to increase production or reticulocytes and red blood cells in the dog or cat.

16 Claims, 9 Drawing Sheets

CANINE ERYTHROPOIETIN GENE AND RECOMBINANT PROTEIN

Matter enclosed in heavy brackets [ ] appears in the original patent but forms no part of this reissue specification; matter printed in italics indicates the additions made by reissue.

This application claims the benefit of U.S. Provisional Patent Application Ser. No. 60/082,669, filed Apr. 22, 1998.

FIELD OF THE INVENTION

The present invention relates to recombinant canine erythropoietin and its use in methods for providing erythropoietin therapy to a dog or cat.

BACKGROUND OF THE INVENTION

Erythropoietin is a glycosylated protein that stimulates red blood cell production. It is produced by interstitial and capillary endotelial cells in the renal cortex and transported in the blood to the bone marrow. Koury et al., "Localization of Erythropoietin Synthesizing Cells in Murine Kidneys by in situ Hybridization," Blood, 71:524–527 (1988); Eschbach, "The Anemia of Chronic Renal Failure: Pathophysiology and the Effects of Recombinant Erythropoietin," Kidneys Int., 35:134–148(1989). The hormone's biological activity involves a direct receptor-mediated stimulation of the maturation and replication of late erythroid progenitor cells, proerythroblasts, and erythroblasts. Mufson et al., "Binding and Internalization of Recombinant Human Erythropoietin in Murine Erythroid Precursor Cells," Blood, 69:1485–1490 (1987); Krantz et al., "Specific Binding of Erythropoietin to Spleen Cells Infected with the Anemia Strain of Friend Virus," Proc. Natl. Acad. Sci. USA, 81:7574–7578 (1984). Synthesis of erythropoietin is stimulated in response to tissue hypoxia mediated by intracellular aerobic metabolism. Erslev, "Physiologic Controls of Red Cell Production," Blood, 10:954–959 (1955). The primary protein structure of human erythropoietin includes a 27 amino acid signal peptide and a 166 amino acid mature protein. Lin et al., "Cloning and Expression of the Human Erythropoietin Gene," Proc. Natl. Acad. Sci. USA, 82:7580–7584 (1985). Predicted molecular weight of 18.4 kDa is substantially less than the 32-kDa observed when erythropoietin is purified directly from blood or urine. The difference is due to glycosylation, three N-linked sugar chains at Asn, 24, 38, and 83, and an O-linked mucin-like moiety at Ser 126. Lai et al., "Structural Characterization of Human Erythropoietin," J. Biol. Chem., 261:3116–3121 (1986). Compared to human, the amino acid sequences of mouse and monkey erythropoietin are 80 and 92% identical, respectively. McDonald et al., "Cloning, Sequencing, and Evolutionary Analysis of the Mouse Erythropoietin Gene," Molecular and Cellular Biology, 6:842–848 (1986): Shoemaker et al., "Murine Erythropoietin Gene: Cloning, Expression, and Human Gene Homology," Molecular and Cellular Biology, 6:849–858 (1986); Lin et al., "Monkey Erythropoietin Gene: Cloning, Expression and Comparison with the Human Erythropoietin Gene," Gene, 44:201–209 (1986). The basic erythropoietin gene structure, five exons and four introns, is conserved.

Recombinant human erythropoietin (rhEPO) synthesized in Chinese Hamster Ovary (CHO) cells is produced commercially (Epogen®, Amgen, Inc. Thousand Oaks, Calif.) and widely used to support red blood cell production in people suffering from anemia secondary to chronic renal disease. Eschbach, "The Anemia of Chronic Renal Failure: Pathophysiology and the Effects of Recombinant Erythropoietin." Kidney Int., 35:134–148 (1989); Eschbach et al., "Treatment of the Anemia of Progressive Renal Failure with Recombinant Human Erythropoietin," N. Engl. J. Med., 321:158–163 (1989). Although the pathogenosis of the anemia is multifactorial, compensatory failure by the bone marrow to replace red blood cells largely involves a loss of functional renal tissue and a drop in endogenous erythropoietin production. Eschbach, "The Anemia of Chronic Renal Failure: Pathophysiology and the Effects of Recombinant Erythropoietin," Kidney Int., 35:134–148 (1989); King et al., "Anemia of Chronic Renal Failure in Dogs," J. Vet. Int. Med., 6:264–270 (1992). Synthesis of rhEPO for clinical use in restricted to eukaryotic cells due to the requirement of post-translational glycosylation for in vivo stability and bioactivity of the hormone. Takeuchi et al., "Structures and Functional Roles of the Sugar Chains of Human Erythropoietins," Glycobiology, 1:337–346 (1991). Devoid of sugars or even the terminal sialic acid residues, erythropoietin is rapidly cleared and metabolized by the liver. Spivak et al., "The in vivo Metabolism of Recombinant Human Erythropoietin in the Rat," Blood, 73:90–99 (1989).

Nonregenerative anemia, characterized by an inadequate production of new red blood cells, is a frequent and serious complication of kidney failure, certain types of cancer, and other chronic diseases in companion animals.

Chronic renal failure is a progressive and irreversible deterioration of kidney function that is a common and frustrating clinical problem in veterinary medicine. Although usually considered a disease of older animals, chronic renal failure is also encountered congenitally as familial renal disease (e.g., in the Norwegian elkhoud, Cocker spaniel, Samoyed, Doberman pinscher, Lhasa apso, Shih Tzu, golden retriever) (Finco, "Congenital, Inherited and Familial Renal Diseases," In: Canine and Feline Nephrology and Urology. Osborne et al., (eds.), Baltimore: Williams & Wilkins, pages 471–483 (1995)) and in other young animals through nephrotoxic or infection mechanisms. Polzin et al., "Diseases of the Kidneys and Ureters," In: Textbook of Veterinary Internal Medicine, Ettinger (ed), Philadelphia: WB Saunders Company. pp. 1962–2046 (1989): Krawiec. "Renal Failure in Immature Dogs." J. Amer. Anim. Hosp. Assoc. 23:101–107 (1987). Despite a poor long-term prognosis, many dogs and cats with chronic renal failure are medically managed for years with special diets, phosphate binders, and antacids. Eventually, however, this conventional therapy fails to control the clinical signs of renal failure. Cowgill et al., "Veterinary Applications of Hemodialysis," In: Kirk's Current Veterinary Therapy, 12th ed., Bonagura et al., (eds.), Philadelphia: W B Saunders, pages 975–977 (1995). For these animals, intermittent hemodialysis has improved survival by decreasing the uremic toxins that accumulate during renal failure. Operational dialysis units are already available in several veterinary centers across the country, and expanded use of hemodialysis in the management of renal failure in veterinary medicine is expected.

Nevertheless, even though dialysis ameliorates the uremia in canine and feline patients, lethargy, weakness, and inappetence resulting from the anemia of chronic renal failure persist. In fact, the anemia may even be compounded by blood loss in the dialyzer. Eschbach et al., "Iron Balance in Hemodialysis Patients," Ann. Int. Med., 87:710–713 (1977). Erythropoietin treatment has become an essential component of the therapy for animals receiving hemodialysis. Even with the life-threatening risk of red cell aplasia, rhEPO is used because it represents the only erythropoietin-replacement option currently available.

Lymphosarcoma (also known as lymphoma or malignant lymphoma) is a common cancer in dogs. Although the exact cause is unknown, certain breeds including Boxer, Basset hound, St. Bernard, Scottish terrier, Airedale terrier, English bulldog, and Labrador retriever have a predisposition for development of this cancer. Nelson et al., Essentials of Small Animal Internal Medicine. St. Louis: Mosby-Year Book, Inc., pages 861–870 (1992). Treatment of lymphosarcoma consists of various chemotherapy protocols (typically utilizing vincristine, cyclophosphamide, doxorubicin, and prednosone) that result in high remission rates and allow survival for approximately 6–12 months.

Nonregenerative anemia is a common hematologic finding in dogs with lymphosarcoma. Nelson et al., Essentials of Small Animal Internal Medicine, St. Louis: Mosby-Year Book, Inc, pages 861–870 (1992); Lucroy, et al., "Anaemia Associated with Canine Lymphoma," Comp. Haematol. Int'l 8:1–6 (1998). The anemia may be encountered during the initial diagnostic evaluation, or may develop during chemotherapy. Similarly, human cancer patients are often anemic, Miller et al., "Decreased Erythropoietin Response in Patients with the Anemia of Cancer." N. Engl. J. Med., 322:1689–1692 (1990); Moliterrio et al., "Anemia of Cancer," Hematol. Oncol. Clin. of N. Am., 10:345–363, (1996). Although the pathogenesis of the anemia of cancer is multifactorial, three major variables identified are: 1) the inhibition of erythropoietin production and bioactivity by inflammatory cytokines and chemotherapeutic drugs; 2) direct inhibition of erythroid progenitors by cytokines; and 3) impaired iron metabolism. Moliterrio et al., "Anemia of Cancer," Hematol. Oncol. Clin. of N. Am., 10:345–363 (1996); Schapira et al., "Serum Erythropoietin Levels in Patients Receiving Intensive Chemotherapy and Radiotherapy," Blood, 76:2354–2359 (1990); Means et al., "Progress in Understanding the Patheogenesis of the Anemia of Chronic Disease," Blood, 80:1639–1647 (1992); Lacome, "Resistance to Erythropoietin." N. Eng. J. Med., 334: 660–662 (1996); Beguin, "Erythropoietin and the Anemia of Cancer," Acta. Clinica. Belgica, 59:36–52 (1996); Mittelman, "Anemia of Cancer: Pathogenesis and Treatment with Recombinant Erythropoietin," Isr. J. Med. Sci., 32:1201–1206 (1996). Consistent with these etiologic variables is clinical data demonstrating that the anemia of cancer in 32–85% of human patients (depending on the cancer type) responds to pharmacologic doses of rhEPO. Mittelman, "Anemia of Cancer: Pathogenesis and Treatment with Recombinant Erythropoietin," Isr. J. Med. Sci., 321201–1206 (1996); Spivak, "Recombinant Human Erythropoietin and the Anemia of Cancer," Blood, 84:997–1004 (1994); Henry, "Recombinant Human Erythropoietin Treatment of Anemia Cancer Patients," Cancer Practice, 4:180–184 (1996). Furthermore, in vitro studies demonstrate a reversal of cytokine-mediated inhibition of erythropoiesis with increased concentrations of rhEPO. Means et al., "Inhibition of Human Erythroid Colony-Forming Units by Gamma Interferon can be Corrected by Recombinant Human Erythropoietin." Blood, 78:2564–2567 (1991). However, treatment with a safe "non-immunogenic" preparation of exogenous erythropoietin to alleviate the anemia associated with cancer and chemotherapy in dogs or cats has not been possible.

As noted above, erythropoietin therapy is often indicated for the management of nonregenerative anemia. In cases of primary erythropoietin deficiency, as in anemia secondary to chronic renal failure, erythropoietin therapy may become essential for life. The only opinion currently available to veterinarians is rhEPO, with its inherent risk of immunogenicity. Cowgill, "Erythropoietin: Its Use in the Treatment of Chronic Renal Failure in Dogs and Cats," Proceedings of the 15th Annual Waltham/OSU Symposium for the Treatment of Small Animal Diseases. Ohio State University, pages 65–71 (1991): Giger, "Erythropoietin and Its Clinical Use," Compend. Contin. Ed. Pract. Vet., 14:25–34 (1992); Cowgill, "Medical Management of the Anemia of Chronic Renal Failure." In: Canine and Feline Nephrology and Urology, Osborne, et al., (eds.), Baltimore: Williams and Wilkins, pages 539–554 (1995); Cowgill et al., "Use of Recombinant Human Erythropoietin for Management of Anemia in Dogs and Cats with Renal Failure. J. Am. Vet. Med. Assoc., 212:521–528 (1998); Stokol et al., "Pure Red Cell Aplasia After Recombinant Human Erythropoietin Treatment in Normal Beagle Dogs," Vet. Pathol., 34:474 (1997). When dogs develop red cell aplasia secondary to rhEPO, continued therapy is contraindicated for two reasons. First, the in vivo bioactivity of rhEPO is blocked, most likely because it no longer even reaches the erythroid progenitor target cells in the bone marrow. Second, the rhEPO therapy is casually associated with the red cell aplasia. Spontaneous recovery of the bone marrow is possible with cessation of the rhEPO treatments. Unfortunately, in many of the clinical cases where either the production or bioactivity of endogenous erythropoietin is compromised by the patient's primary disease, this spontaneous recovery of erythropoiesis never develops or is so inadequate that the red cell aplasia proves to be fatal.

In dogs and cats, the progressive clinical syndrome associated with chronic diseases, such as renal failure, also includes development of a nonregenerative anemia. In parallel to the human literature, studies have documented low serum concentrations of erythropoietin despite the anemia. King et al., "Anemia of Chronic Renal Failure in Dogs," J. Vet. Int. Med., 6:264–270 (1992). Therapeutic use of rhEPO in dogs and cats with anemia secondary to chronic renal failure results in a rapid and significant red blood cell response. Cowgill, "Erythropoietin: Its Use in the Treatment of Chronic Renal Failure in Dogs and Cats." Proceedings of the 15th Annual Waltham/OSU Symposium for the Treatment of Small Animal Diseases. Ohio State University, pages 65–71 (1991); Giger, "Erythropoietin and Its Clinical use," Compend. Cantin. Ed. Pract. Vet., 14:14 25–34 (1992); Cowgill, "Medical Management of the Anemia of Chronic Renal Failure," In: Canine and Feline Nephrology and Urology. Osborne et al. (eds.). Baltimore: Williams and Wilkins, pages 539–554 (1995); Cowgill et al., "Use of Recombinant Human Erythropoietin for Management of Anemia in Dogs and Cats with Renal Failure." J. Am. Vet. Med. Assoc., 212:521–528 (1998). Depending on the dose administered, hematocrit and hemoglobin values can be restored to a normal range within several weeks and treated animals display increased alertness, physical strength, appetite, and overall attitude. These findings strongly suggest that the persistent anemia contributes significantly to some of the clinical manifestations of chronic renal failure. Unfortunately, the red blood cell status of both dogs and cats often declines in 1 to 4 months despite continued rhEPO therapy. Therapeutic failure of rhEPO in companion animals, estimated with an incidence between 20 and 50%, appears to result from interspecies variation in erythropoietin structure and the appearance of antibodies against the human protein. The ability of rhEPO to bind target receptors on erythroid progenitor cells is conserved, but the human protein is frequently recognized as foreign by the immune system of animals. Cowgill, "Erythropoietin: Its Use in the Treatment of Chronic Renal Failure in Dogs and Cats," Proceedings of the 15th Annual Waltham/OSU Symposium for the Treatment of Small Animal Diseases. Ohio State University, pages 65–71 (1991); Giger, "Erythropoietin and Its Clinical Use," Compend. Contin. Edg., Pract. Vet., 14:25–34 (1992); Cowgill, "Medical Management of the Anemia of Chronic Renal Failure," In: Canine and Feline Nephrology and Urology. Osborne et al., (eds.), Baltimore: Williams and Wilkins, pages 539–554 (1995); Cowgill et al., "Use of Recombinant Human Erythropoietin for Management of Anemia in Dogs and Cats with Renal Failure," J. Am. Vet. Med. Assoc., 212:521–528 (1998).

Anti-rhEPO antibodies are thought not only to effectively block rhEPO's bioactivity, but also have the potential to cross react with residual endogenous erythropoietin and lead to a pure red cell aplasia. This problem of immunogenicity can be life threatening and has severely limited the therapeutic potential of rhEPO for veterinary applications. The concept of erythropoietin replacement is appropriate for comparison animals, the problem is the immunogenicity of rhEPO.

The cDNA sequences for a number of mammalian erythropoietin genes are disclosed in Wen, et al., "Erythropoietin Structure-Function Relationships: High Degree of Sequence Homology Among Mammals," Blood 82(5):1507–16 (1993). Although the nucleotide sequence for dog is disclosed, that sequence is missing the coding information for the first four codons of canine erythropoitin, which is critical for recombinant production of this protein.

The present invention is directed to overcoming the above-noted deficiencies in the prior art.

SUMMARY OF THE INVENTION

One aspect of the present invention is an isolated nucleic acid molecule encoding canine erythropoietin.

The present invention also relates to an isolated canine erythropoietin protein or polypeptide.

Another aspect of the present invention is a method for providing erythropoietin therapy to a dog including administering recombinant canine erythropoietin to a dog, in need of erythropoietin therapy in an amount sufficient to increase production of reticuloyctes and red blood cells in the dog.

The present invention also relates to a method for providing erythropoietin therapy to a cat including administering recombinant canine erythropoietin to a cat in need of erythropoietin therapy in an amount sufficient to increase production of reticuloyctes and red bloods cells in the cat.

Recombinant canine erythropoietin ("rcEPO") exhibits comparable biological activity of rhEPO. Further, through the absence (dog) or significant reduction (cat) of the interspecies variation in protein structure, rcEPO stimulates erythropoiesis while avoiding the immunogenicity problems that occur with rhEPO. Thus, the availability of rcEPO should provide veterinarians and pet owners with a valuable therapeutic modality to improve the quality of life for dogs and cats suffering from the anemia of chronic renal failure.

DETAILED DESCRIPTION OF THE INVENTION

Figure 1:
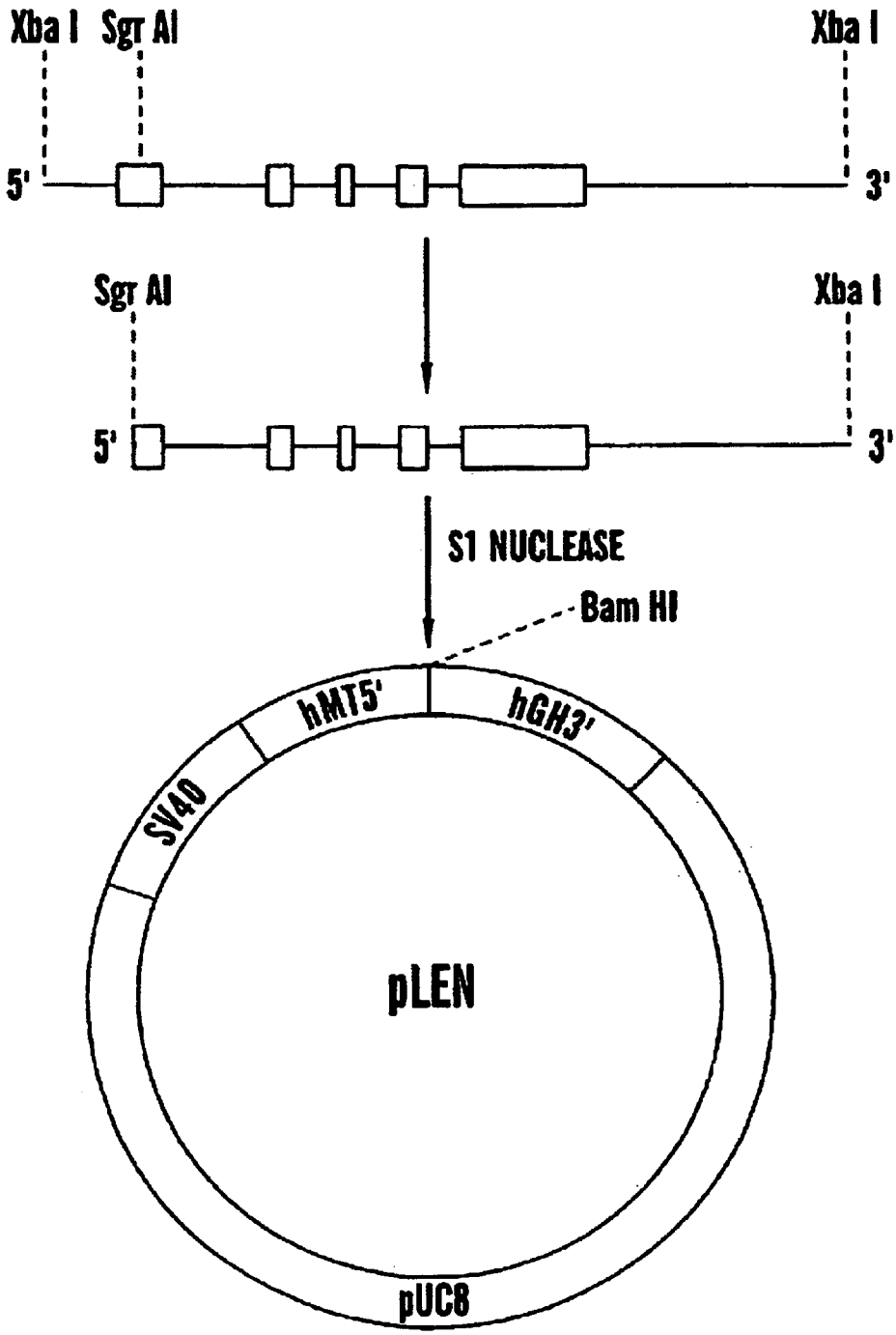
FIG. 1 shows the construction of a canine EPO ("cEPO") expression plasmid. The cEPO gene contained within a 4.4 kb Xba I fragment was digested with the restriction enzyme Sgr A1 to remove an ATG located 66 bases upstream of the translational start site. Identity of the cEPO translational start and stop codons were deduced by comparison to published erythropoietin sequence data for mouse, monkey, and human. The Sgr A1-Xba I fragment was then blunt ended with S1 nuclease and ligated into the BamHI site of the eukaryotic expression vector pLEN that was similarly blund ended. In this construct, constitutive transcription of cEPO is driven by SV40 enhancer and human metallothionein promoter sequences.

One aspect of the present invention is an isolated nucleic acid molecule encoding canine erythropoietin. The present invention provides the full length genomic sequence of the canine erythropoietin gene.

In a preferred embodiment, the isolated nucleic acid molecule is capable of being expressed in transfected cells and which hybridize to a nucleic acid molecule having a nucleotide sequence of SEQ ID No. 1 under stringent conditions but not to a nucleic acid molecule encoding human erythropoietin under identical conditions.

The DNA molecule which encodes rcEPO comprises the nucleotide sequence corresponding to SEQ ID No. 1 as follows (codons are given as triplicate nucleotides and noncoding introls and flanking regions are given as continuous nucleotides):

```
TCTAGAACAAGTACTGGGATTGCGAGAAGGAAGGCAACTTGCCTCTGCCCGCACCTTCCC

GGCTTCCAAGGCTAGTTGCCCCGCAGGCACCAGGCACCGGCGCTCCCAGCTCGATCCCCC

GCCCAGGACTGGGACGCACCCCTCCCCCCGGGGGGAGGGGGGCGGGAGCCTCGGGGTCCC

CGGCCTTTCCCAGAATGGCACCCCTCCCGCGGGTGCGCACCCAGCCGCGCCTCCCACAAC

CCGGGGTCAGACTGGCGGACCCGCGTCCCGCTCCGCGCCTGCTGCCGCGCCTGCTGCCGC

TCTGCTCCCGCCCCGGCGAGCCCCCGACCCAGGCGTCCTCCCCCGGTCTGACCCCTCTGG

CCCTTACCTCTGGCGACCCCTCACGCACACAGCCTGCCCCCCACCCCCACACACGCACGC

ACACATGCTGATAACAGCCCCGACCCCCGGCCGAGCCGCAGTCCCCGGGCCAACCCCGGC

CGGTCGCCGCGCGCCTGTCCTCGCGGACCCTGGCCGAGAGCCCTGCGCTCGCTCTGCGCG

ACCCCGGCTCGGCGGCCCCTGGACGGTGGCCCCCTCCTTCGGACCGTGGGGCCGGCCCTG

CCCCGCCGCGCTTCCCGGGATGAGGGCTCCCGGCGAGGGCGCCGGCGGAGCCCCTGGTCG

CTGAGCGGCCGACGGAGGCGCGGAG

ATG GGG GCG TGC G

GTGAGTACTCGCCGGCCGGAGGAGCCCCCGCCCGCTCGGGCCCCTGTTTGAGCAAGAATT

TACCGCTGGGGCCCCGAGGTGGCTGGGTTCAAGGACCGACGACTTGCCAAGGACCCCGGA

AGGGCAAGGGGGGTGGCCCAGCCCCCACGTGCCGGCAGGGCTTAGGGAGCCCCTAGGAAA

GGTGAAATCTGACCTGGACACGGGGATGCCGTTTGGGGGTTCAGGGAGCCGAGGGGCTGC

CACGTGCGTGGGGAGAAGGCTGATACCTGGGTCTTGGAGCAATCACCGGGATCTGCCAGA

GGGGAAGCCTCAGTCACGCCGGGATTGAAGTTTGGCCGGGAGAAGTGGATGCCGGTAGTT

TGGGGGGTGGGCTGTGCGCGCAGCAGCGGCCGGATTGAATGAAGGCAGGGCAGGCAGAAC

CTGAACGCTGGGAAGGTGGGGGTCGGGCGCGACTAGTTGGGGGCAGAGGAGCGGGATGTG

TGAACCTGCCCCTCCAAACCCACACAGTCAGCCTGGCACTCTTTTCCAG

AA TGT CCT GCC CTG TTC CTT TTG CTG TCT TTG CTG CTG CTT CCT

CTG GGC CTC CCA GTC CTG GGC GCC CCC CCT CGC CTC ATT TGT GAC

AGC CGG GTC CTG GAG AGA TAC ATC CTG GAG GCC AGG GAG GCC GAA

AAT GTC ACG

GTGAGGGTCCCACCTCAGGACATTCTCAGTAGTCCAGGGGTGTCCTCCAAGATCTGGGAA
```

-continued

CCTGAGCCCCTTCGTTCAGAGATGGAGATGGGAAGCCAGAGCCCTCAGGAAAAATGATAA

AAGTGGTAGCCCCTCAATGCATGCCTGGAAGCTAGATCAGGGGCAAAGCTGGAGGGAGCT

CTTGGGGAGCCTGACACCCCCTTCCCCCCGACCTGGGCTCATGCATTTCAG

ATG GGC TGT GCT CAA GGC TGC AGC TTC AGT GAG AAT ATC ACC GTC

CCA GAC ACC AAG GTT AAT TTC TAT ACC TGG AAG AGG ATG GAT

GTGAGTTTATTTTTCCCCTCTACTTGGACAGTCTTGTTTTGCTTACCTGATGGGGTGGGA

GGGAGTACCATAGAAGAAGCTGAGGGCTCAATGCAATATGTTTACTCATTTGTTCTTTGT

TCATTCATTAATTCATTCATTCAATGAAACTGATTCCAAGCCTTCATTTTGCTCAGCTTG

GTGCTTGGGGCTGCTGAGAGGGAGGGGCTGGCCTGGGCCGCTGACTATAAGTCGCCATTC

CCTTTAG

GTT GGG CAG CAG GCC TTG GAA GTC TGG CAG GGC CTG GCA CTG CTC

TCA GAA GCC ATC CTG CGG GGT CAG GCC CTG TTG GCC AAC GCC TCC

CAG CCA TCT GAG ACT CCG CAG CTG CAT GTG GAC AAA GCC GTC AGC

AGC CTG CGC AGC CTC ACC TCT CTG CTT CGG GCG CTG GGA GCC CAG

GTGGGTAGAAGCCTCCCTTGCACTTCTGCTCCAAGGGCCCTGCCAAGAAATACTGAGACC

CCACTGGACCTCCTCATCCCCCCTCCAATTCTGTCCTCCATCCCATCTCCCACCAGGGTC

CTGGGCACTTCGGTAACCTTCTCTTCTCTCCTTGTCAG

AAG GAG GCC ATG TCC CTT CCA GAG GAA GCC TCT CCT GCT CCA CTC

CGA ACA TTC ACT GTT GAT ACT TTG TGC AAA CTT TTC CGA ATC TAC

TCC AAT TTC CTC CGT GGA AAG CTG ACA CTG TAC ACA GGG GAG GCC

TGA AGA AGA GGA GAC AGG TGA

CCAGGTGCTCCCACCCCAGGCACATCCACCACCTCACTCACTACCACTGCCTGGGCCACG

CCTCTGCACCACCACTCCTGACCCCTGTCCAGGGGTGATCTGCTCAGCACCACCCTGTCC

CTTGGACACTCCACGGCCAGTGGTGATATCTCAAGGGCCAGAGGAACTGTCCAGAGCTCA

AATCAGATCTAAGGATGTCACAGTGCCAGCCTGAGGCCCGAAGCAGGAGGAATTCGGAGG

AAATCAGCTCAAACTTGGGGACAGAGCCTTGCTCGGGAGACTCACCTCGGTGCCCTGCCG

AACAGTGATGCCAGGACAAGCTGGAGGGCAATTGCCGATTTTTTGCACCTATCAGGGAGA

GACAGGAGAGGCTAGAGAATCTAGGTGGCAAGCCATAAATTCTCTAGGTCTCGTGGGTCT

CCTATGACAGCAAGAGCCCACTGGCAAAGGGTGGTGGCAGCCATGGAGATGGGATAGGGG

CTGGCCCCTGGCTCTCATTGGGTCCAAGTTTTGTGTATTTTTCAATCTCATTGGCAGAAA

CTGAAACCACAACATGGCTCTTGACTTTTCTGTTTTCCCTGGGATCCTCCTACTTCCCTG

GCCCTGCTCCGGCCCTGGCAGCAGGCCACAGTCCTGGAAAACTAGAGGTGGAGGGGGTCG

GCCCTACGTGCTGCCTCTCATGGTCTATCTGACCTCTTGACCCCACTGGGTCTGAGGCCA

CAAGCTCTGCCCACGCTGGTCAATAAGGTGGTTCTATTCAAGGCTGTTCCTCAGTAGGCA

GTTGGCAACCCTCTGTAGTGAGCTACAGCTGCCATCAAGGAAACAGGAGCCAGGAGGAAG

AGCCCCTTTGGGGGCTGGTGGGAGTTCCCAGTCCTGGACCCTGGACCCTTATTATTTCTC

ACTTCTCCATAGTGCTTTTGACTAAAGCCACATTCCCACATCAGCCTTTGCCACCTCTAA

ATCCAGCTGACCCTTTTCCTTGCCTGAGGATGGTCAAGGCAAGGAAATGCTCTACCCCAA

AACTTGCAGAAGGAGCCACGTTCCCCAAAAGCGGTCTCACTGAGCACTCACTCTGTGCCC

AGGGCTATTCTAGGTGGTTCACTTACATGACATTTTATTCCTTGCACAGCCTGATGAGAA

-continued

AGTTTCCACTGTCATTCCCAGATGAGAAGTAAACTGCCCAAAGCCAAGACAACAGGAATC

CCCAATGGCCCCAGCTCTTATCCCTTCCCTCTTCAGCTTATTCTTCCACATAACCCCTAC

CTGCTCCCTGCTCCCCTGGGATGGGAGACACAGAACAGACTAACTCAGCTCCCGCTCTCC

ATCCCTACTAATAATTTTACCCAGTACTCCAACATTCCACTTCAAATTCCTTCCCAGAGG

GATGCCTTGGTGGCTCAGTGGTAGAGTGTCTGCCTTTGCTCAGGTCGTGATCCCCAGGTC

CAGAGATTGAGTCCTGCATCAGGCTCCCTGCAGAGAGCCCAATCCTGCCATTATCATATG

TGTGGGGATCAGCCTTTCTGCTCATATCACAAAACTTAGAGAAGTCAGCCTGCATCCCTG

AAAATATCAAAAGAAAAAGAATTTTTGCAATCTGCAGGAGGACAAATGATGGGTCGGTTG

GGGGATTGGATGGTATGTGCTAAATATATGTGTGTGTGCTGGGGGGCCGTGCCAAGCGTG

GTGGGAGGAATCAAAGGAGAGGTGGACCCAAAGGAGAATTCCCCCCTCCTCCCCTGCCTG

GCCAACTCAGTTCCTAGGGTATACTGCCCTCTTCAGGCCCCACTGGAAAATGTTAGAGAA

ATACACAAGTCAAAGAGCCCTTAGGTCTCTGATTATTCTTTGCACATTTCAATAAAAATT

TGTATTACAGTTTCCACAGATGGCATCTGGTTCTTGCCCCACTGCTGTGAAACAGTAAGG

GAGGAATCTGTCTCTCTCGCTGNCAAAATCGAAGCTAAGAGAGGTGTCCAAGGCATGCAG

CTAATAATGGTAGCTAGGACCTGAACACAAGGTTTAGGAATCGTAACCTCCAAGCCCATC

TTAGCCTGATGTGTCATCTAGA

In a most preferred embodiment, the nucleic acid molecule comprises the nucleotide sequence of SEQ ID No. 1.

The canine erythropoietin cDNA sequence is given as SEQ. ID. No. 2, as follows:

ATG GGG GCG TGC GAA TGT CCT GCC CTG TTC CTT TTG CTG TCT TTG

CTG CTG CTT CCT CTG GGC CTC CCA GTC CTG GGC GCC CCC CCT CGC

CTC ATT TGT GAC AGC CGG GTC CTG GAG AGA TAC ATC CTG GAG GCC

AGG GAG GCC GAA AAT GTC ACG ATG GGC TGT GCT CAA GGC TGC AGC

TTC AGT GAG AAT ATC ACC GTC CCA GAC ACC AAG GTT AAT TTC TAT

ACC TGG AAG AGG ATG GAT GTT GGG CAG CAG GCC TTG CAA GTC TGG

CAG GGC CTG GCA CTG CTC TCA GAA GCC ATC CTG CGG GGT CAG GCC

CTG TTG GCC AAC GCC TCC CAG CCA TCT GAG ACT CCG CAG CTG CAT

GTG GAC AAA GCC GTC AGC AGC CTG CGC AGC CTC ACC TCT CTG CTT

CGG GCG CTG GGA GCC CAG AAG GAG GCC ATG TCC CTT CCA GAG GAA

GCC TCT CCT GCT CCA CTC CGA ACA TTC ACT GTT GAT ACT TTG TGC

AAA CTT TTC CGA ATC TAC TCC AAT TTC CTC CGT GGA AAG CTG ACA

CTG TAC ACA GGG GAG GCC TGC AGA AGA GGA GAC AGG TGA

In a preferred embodiment, the nucleic acid molecule encodes the amino acid sequence of SEQ ID No. 3 as follows (shown under the cDNa open reading frame sequence):

Met Gly Ala Cys Glu Cys Pro Ala Leu Phe Leu Leu Leu Ser<

Leu Leu Leu Leu Pro Leu Gly Leu Pro Val Leu Gly Ala Pro<

-continued

```
Pro Arg Leu Ile Cys Asp Ser Arg Val Leu Glu Arg Tyr Ile<

Leu Glu Ala Arg Glu Ala Glu Asn Val Thr Met Gly Cys Ala<

Gln Gly Cys Ser Phe Ser Glu Asn Ile Thr Val Pro Asp Thr<

Lys Val Asn Phe Tyr Thr Trp Lys Arg Met Asp Val Gly Gln<

Gln Ala Leu Glu Val Trp Gln Gly Leu Ala Leu Leu Ser Glu<

Ala Ile Leu Arg Gly Gln Ala Leu Leu Ala Asn Ala Ser Gln<

Pro Ser Glu Thr Pro Gln Leu His Val Asp Lys Ala Val Ser<

Ser Leu Arg Ser Leu Thr Ser Leu Leu Arg Ala Leu Gly Ala<

Gln Lys Glu Ala Met Ser Leu Pro Glu Glu Ala Ser Pro Ala<

Pro Leu Arg Thr Phe Thr Val Asp Thr Leu Cys Lys Leu Phe<

Arg Ile Tyr Ser Asn Phe Leu Arg Gly Lys Leu Thr Leu Tyr<

Thr Gly Glu Ala Cys Arg Arg Gly Asp Arg
```

Suitable nucleic acid molecules include those nucleic acid molecules encoding an amino acid of a protein or polypeptide sufficiently to duplicative of canine erythropoietin and having a nucleotide sequence which is at least 95% homologous and preferably 98% homologous to the nucleotide sequence of canine erythropoietin ("EPO") (as shown in SEQ ID No. 1).

While the nucleotide sequence is at least 95% homologous as determined by the TBLAST Program (Altschul. S. F., et al., "Basic Local Alignment Search Tool," J. Mol. Biol. 215:403–410 (1990), which is hereby incorporated by reference) using the default parameters, nucleotide identity is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the canine EPO nucleotide and/or amino acid sequences which do not alter the function of the resulting canine EPO.

Alternatively, suitable DNA sequences may be identified by hybridization to SEQ ID No. 1 under stringent conditions. Preferably, suitable sequences would hybridize to SEQ ID Nos 1 under highly stringent conditions where a nucleic acid encoding human EPO would not hybridize. For example, sequences can be isolated that hybridize to a DNA molecule comprising a nucleotide sequence of 50 continuous bases of SEQ ID No. 1 under stringent conditions characterized by a hybridization buffer comprising 0.9M sodium citrate ("SSC") buffer at a temperature of 65° C. and remaining) bound when subject to washing with the SSC buffer at 65° C.; and preferably in a hybridization buffer comprising 20% formamide in 0.9M saline/0.09M SSC buffer at a temperature of 75° C., and remaining bound when subject to washing at 42° C. with 0.2×SSC buffer at 75° C.

The DNA molecule encoding the canine EPO protein or polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to pLEN, the pCDN series (Invitrogen), pRc/CMV2 (Invitrogen), and pNeoEGFP (Clontech), the following viral vectors such as lambda vector system gt11, gt WES.tb, Charon 4, and plasmid vectors such as pBR322, pBR325, ACTC177, pACY1084, pUC8, pUC9, pUC18, pUC19, pLG339, pR290, pKC37, pKC101, SV 40, pBluescript II SK +/− or KS +/− (see "Statagene Cloning Systems" Catalog (1993) from statagene, La Jolla, Calif. whic is hereby incorporated by reference), pQE, pIH821, pGEx, pET series (see Studier et al., "Use of T7 RNA Polymerase to Direct Expression of Cloned Genes," Gene Expression Technology, vol. 185 (1990), which is herein incorporated by reference), and any derivatives thereof. In a preferred embodiment, the vector is eukaryotic expression vector pLEN. Recombinant molecules can be introduced into cells via transformation, transduction, conjugation, mobilization, or electroporation. The DNA sequences are cloned into the vector using standard cloning procedures in the art, as described by Maniatis et al., Molecular Cloning: A Laboratory Manual, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cells used. Host-vector systems include but are not limited to the following: subcloning a eukaryotic expression vector into mammalian cell systems; microorganisms such as yeast containing yeast vectors, mammalian cell systems infected with virus (e.g., vaccinia virus, adenovirus, etc.); and insect cell systems infected with virus (e.g., baculovirus). The expression elements of these vectors vary in their strength and specification. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of procalyotic promoters. Furthermore, eukaryotic promoters and accompanying genetic signals may not be recognized in or may not function in a procaryotic system, and, further, procaryotic promoters are not recognized and do not function in eukaryotic cells. Similarly, translation of mRNA in prokaryotes depends upon the presence of the proper procaryotic signals which differ from those of eukaryotes. For a review on maximizing gene expression, see Roberts and Lauer, Methods in Enzymology, 68:473 (1979), which is hereby incorporated by reference.

Promoters vary in their "strength" (i.e. their ability to promote transcription). For the purposes of expressing a cloned gear, it is desirable to use strong promoters in order to obtain a high level of transcription and, hence, expression of the gene. Depending upon the host cell system utilized, any one of a number of suitable promoters may be used. For instance, when cloning in chinese hamster ovary cells, human metallothionein IIA promoter the regulatory sequences from CMV, RSV or SV40, and the like, may be used to direct high levels of transcription of adjacent DNA segments. Additionally, promoters produced recombinant DNA or other synthetioc DNA techniques may be used to provide the transcription of the inserted gene.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals.

Once the isolated DNA molecules encoding the canine EPO proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, mammalian cells (chinese hamster ovary cells, and the like), yeast cells, and insect cells.

The present invention also relates to an isolated canine erythropoietin protein or polypeptide.

In a preferred embodiment, the protein or polypeptide is sufficiently duplicative of canine erythropoietin to have the biological property of causing bone marrow cells to increase production of reticuloyctes and red blood cells and to have the immunological property of not provoking an immune response in a dog.

Preferably, the protein or polypeptide has an amino acid sequence of SEQ ID No. 3.

Fragments of the above polypeptides or proteins are also encompassed by the present invention.

Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for activity according to the procedures described below.

As an alternative, fragments of replication proteins can be produced by digestion of a full-length replication protein with proteolytic enzymes like chymotrypsin or Staphylococcus proteinase A, or trypsin. Different proteolytic enzymes are likely to cleave replication proteins at different sites based on the amino acid sequence of the protein. Some of the fragments that result from proteolysis may be active.

In another approach, based on knowledge of the primary structure of the protein, fragments of a replication protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences of replication proteins being produced. Alternatively, subjecting a full length replication protein to high temperatures and pressures will produce fragments. These fragments can then be separated by conventional procedures (e.g., chromatography, SDS-PAGE).

Variants may also (or alternatively) by modified by, for example, the deletion or addition of nucleotides that have minimal influence on the properties, secondary structure and hydropathic nature of the encoded polypeptide. For example, the nucleotides encoding a polypeptide may be conjugated to a signal (or leader) sequence at the N-terminal end of the protein which co-translationally or post-translationally directs transfer of the protein. The nucleotide sequence may also be altered so that the encoded polypeptide is conjugated to a linker or other sequence for ease of synthesis, purification, or identification of the polypeptide.

The protein or polypeptide of the present invention is preferably produced in purified form (preferably, at least about 80%, more preferably 90%, pure) by conventional techniques. Published methods that have been used to purify human erythropoietin from the urine or sickle cell anemia patients should be applicable to the purification of rcEPO from conditioned tissue culture medium. (Miyake et al., "Purification of Human Erythropoictin," J. Biol. Chem., 252:5558–5564 (1977); Krystal et al., "Purification of Human Erythropoietin to Homogeneity by a Rapid Five-Step Procedure," Blood, 67:71–79 (1986), which are hereby incorporated by reference).

In a preferred embodiment, the protein or polypeptide of the present invention is administered in a pharmaceutical composition including an effective amount of the protein or polypeptide of the present invention and a pharmaceutically acceptable diluent, adjuvant, or carrier, as disclosed below.

In a most preferred embodiment, the pharamceutical composition is administered in an effective amount to provide erythropoietin therapy to a dog or cat.

Another aspect of the present invention is a method for providing erythropoietin therapy to a dog including administering recombinant canine erythropoietin to a dog in need of erythropoietin therapy in an amount sufficient to increase production of reticuloyctes and red blood cells in the dog.

In a preferred embodiment, the dog is suffering from anemia, chronic or acute renal failure. In a most preferred embodiment, the dog is suffering from chronic or acute renal failure and the dog is one of the following breeds: Norwegian elkhound, Cocker spaniel, Samoyed, Doberman pinsher, Lhasa apso, Shih Tsu or golden retriever.

In another preferred embodiment, the dog is suffering from cancer. In a more preferred embodiment, the dog is suffering from lymphosarcoma and the dog is one of the following breeds. Boxer, Basset hound, St. Bernard, Scottish terrier, Airedal terrier, English bulldog, and Labrador retriever.

In another embodiment, the dog is suffering from rhEPO induced red cell aplasia.

In another embodiment, the dog is administered recombinant canine erythropoietin prior to undergoing surgery.

Preferably, the recombinant canine erythropoietil ("rcEPO") of the present invention is encoded by a nucleic acid molecule having a nucleotide sequence of SEQ ID No. 1.

Preferably, from about 50 units/kg to about 500 units/kg of rcEPO is administered to the dog to increase production of reticuloyctes and red blood cells in the dog. Most preferably, from about 100 units/kg to about 200 units/kg of rcEPO is administered to the dog.

The rcEPO of the present invention can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. It may be administered alone or with pharmaceutically or physiologcially acceptable carriers excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the rcEPO of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The rcEPO of the present invention may also be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly, for injection solutions.

For use as aerosols, the rcEPO of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The present invention also relates to a method for providing erythropoietin therapy to a cat including administering recombinant canine erythropoietin to a cat in need of erythropoietin therapy in an amount sufficient to increase production of reticuloyctes and red blood cells in the cat.

In a preferred embodiment, the cat is suffering from anemia secondary to chronic or acute renal failure, caiicer, or red cell aplasia. In a most preferred embodiment, the cat is suffering from lymphosarcoma.

In another embodiment, the cat is administered recombinant canine erythropoietin prior to undergoing surgery.

Preferably, the rcEPO is administered to the cat in the same dosage as described above for dogs.

EXAMPLES

Example 1

Isolation and Cloning of Canine Erythropoictin (rcEPO)

The gene encoding canine erythropoietin (cEPO) was isolated from a Lambda DASH genomic library of canine DAN partially digested with Sau3A 1 (Stratagene, La Jolla, Calif.). Approximately one million bacteriophage plaques were screened with a 180 base pair cDNA fragment from exon 4 of cEPO. The cDNA fragment was generated by polymerase chain redaction (PCR) amplification of canine (genomic DNA using 5'-GTTGGGCAGCAGGCCTTGGAAGT (sense) (SEQ ID No. 4) and 5'-CTGGGCTCCCAGCGCCCGAA (antisense) (SEQ ID No. 5) as primers. The primers correspond to bases 232–254 and 392–411 of the partial cEPO cDNA available through GenBank accession number L13027 and published by Wen et al., "Erythropoietin Structure-Function Relationships: High Degree of Sequence Homology Among Mammals," Blood, 82:1507–1516 (1993), which is hereby incorporated by reference) The exon 4 fragment was then subcloned into pGEM-3Zf(+) (Promega, Madison, Wis.), amplified in E. coli strain JM 109 (Promega, Madison, Wis.), re-isolated in large amounts by preparative restriction digests and agarose gel purification, labeled with $^{32}$p-dCTP using random hexanucleotide primers (Prime-a-Gene, Promega, Madison, Wis.), and purified by G-50 Sephadex spin column chromatography (Boehringer Mannheim, Indianapolis, Ind.). A total of 9 genomic clones that hybridized specifically to the exon 4 probe were isolated and plaque purified. Southern blot analyses determined that 8 of these clones contained the entire cEPO coding region within a 4.5 kb Xba I fragment.

An expression plasmid was constructed by subcloning the cEPO gene (extending from an Sgr A1 site located 40 bases upstream of the translational start site to the 3' Xba I site located 2,060 bases downstream of the stop codon) into the Bam H1 site of the eukaryotic expression vector pLEN. Friedman et al., "High Expression in Mammalian Cells Without Amplification," Bio/Technology, 7:359–362 (1989), which is hereby incorporated by reference. Identity of the start and stop codons in the cEPO gene were deduced by comparison to published erythropoictin sequence data for mouse, monkey, and human. Lin et al., "Cloning and Expression of the Human Erythropoietin Gene," Proc. Natl. Acad. Sci. USA, 82:7580–7584 (1985); McDonald et al., "Cloning, Sequencing, and Evolutionary Analysis of the Mouse Erythropoietin Gene," Molecular and Cellular Biology, 6:842–848 (1986); Shoemaker et al., "Murine Erythropoietin Gene: Cloning, Expressions and Human Gene Homology," Molecular and Cellular Biology, 6:849–858 (1986); Lin et al., "Monkey Erythropoietin Gene: Cloning, Expression and Comparison with the Human Erythropoietin Gene," Gene, 44:201–209 (1986), which are hereby incorporated by reference. The cEPO aenomic insert and pLEN vector were both blunt ended with S 1 nuclease prior to ligation. Orientation of recombinants were determined by direct DNA sequence analysis. Constitutive high level transcription of cEPO in this construct was driven by the SV40 enhancer and human metallothionein 11A promoter of pLEN (FIG. 1).

Example 2

Expression of rcEPO and RNA Gel Analyses

A cell culture system for the production of rcEPO was established by cotransfection of the pLEN-cEPO construct with pRSVneo at a 10:1 molar ratio using calcium phosphate coprecipitation into Chinese Hamster Ovary cells (CHO-KI, American Type Culture Collection, Rockville, Md.). Gorman et al., "High Efficiency DNA Mediated Transformation of Primate Cells, Sceince, 221:551–553 (1983); Graham et al., "A New Technique for the Assay of Infectivity of Human Adenovirus 5 DNA," Virology, 52:456–467 (1973), which are hereby incorporated by reference. The cells were maintained at 370° C., 5% $CO_2$/95% air in Dulbecco's modified Eagle's medium (Gibco BRL, Grand Island, N.Y., catalog no. 11,965) supplemented with 10% (v/v) fetal bovine serum. Following transfection, G418 (400 μg/ml) was added to the culture medium to eliminate nontransformants. A total of 122 transformed CHO cell clones were individually isolated and expanded. Relative expression of cEPO in each CHO clone was compared in parallel on a transcriptional level by Nothern blot analyses. (Subsequently, CHO-rcEPO cell lines were adapted to grow in serum free media, greatly simplifying the biochemical purification procedures of rcEPO. This expression system routinely achieved media concentration of rcEPO that exceeded 100 U/ml. Using roller bottles, 20,000 units of rcEPO can be synthesized in a single culture vessel every 24 hours, an amount sufficient to treat a 10 kg dog for two months). Total RNA was isolated by acid guanidinium thiocyanate-phenol-chloroform extraction followed by differential alcohol and salt precipitations and quantified spectrophotometrically. Chomczynski et al., "Single-Step Method of RNA Isolation by Acid Guanidinium Thiocyanate-Phenol-Chloroform Extraction," Anal. Biochem., 162:156–159 (1987), which is hereby incorporated by reference. Each RNA sample (5 μg) was electrophoretically separated through 1.5% agarose, 6.5% formaldehyde, submersed stab gels in buffer (pH 7.0) containing 40 mM MOPS, 10 mM sodium acetate, and 1 mM EDTA. The separated RNAs were then transferred to nylon membranes (Magna Charge, Micron Separations, Inc., Westboro, Mass.) by standard capillary blotting techniques and probed with $^{32}P$ labeled cEPO exon 4 cDNA fragment. Sambrook et al., "Molecular Cloning: A Laboratory Manual, 2d ed., Cold Spring Harbor Laboratory, Cold Spring Harbor, N.Y. (1989), which is hereby incorporated by reference. Relative comparisons of steady state cEPO and mRNA between individual CHO cell clones were determined by direct quantitation of $^{32}P$ decay events from the hybridization membrane (Phosphor Imager, Fuji Bio-Imaging, Stamford, Conn.). These data were then normalized to expression of the housekeeping gene elongation factor Tu (EFTTu) to correct for any variation in RNA loading or transfer efficiency between samples. Levine et al., "Elonation Factor Tu as a Control Gene for mRNA Analysis of Lung Development and Other Differentiation and Growth Regulated Systems," Nucl. Acids Res., 21:4426 (1993), which is hereby incorporated by reference.

Example 3

Protein Analyses by Immunoblotting

Conditioned medium (30 μl) from a high cEPO expressing CHO cell clone was resolved by SDS-15% polyacrylamide gel electrophoresis under reducing conditions in parallel with an equal volume of conditioned medium from control CHO cells and t5 units of rhEPO. Laemmli, "Cleavage of Structural Proteins During the Assembly of the Head of the Bacteriophage T4," Nature, 267:680–685 (1970), which is hereby incorporated by reference. The three samples were analyzed both with and without peptide N-glycosidase F digestion (PNGase F, New England Biolabs, Beverly, Mass.). PNGase F reaction buffers and protocols were supplied by the manufacturer. Following separation, the proteins were transferred by electroblotting at 33 V and 4° C. overnight to a nitrocellulose membrane (Bio-Rad, Hercules, Calif.). The membrane was blocked for 1 hour at room temperature with 5% nonfat milk in 50 mM Tris, 150 mM NaCl buffer (pH 7.4) with 0.05% (v/v) Tween-20 (TBS-T buffer). After rinsing with TBS-T buffer, the membrane was incubated with a monoclonal antibody to human erythropoietin (Genzyme, Cambridge, Mass.) at a dilution of 1:1000 for 1.5 hours at room temperature. The membrane was then rinsed again with TBS-T and bound primary antibody detected with a horseradish peroxidase-linked goat anti-mouse IgG (Sigma, St. Louis, Mo.) at a dilution of 1:8000. The secondary antibody incubation step was 1.5 hours at room temperature. After a final rinse with TBS-T, buffer, peroxidase activity was detected by chemiluminescence (ECL Western blotting detection system. Amersham, Arlington Heights, Ill.) and autoradiography.

Example 4

Erythropoietin Bioassays

The biological activity of rcEPO was examined in vitro using splenic erythroid progenitor cells isolated from phenylhydrazine treated mice. Krystal, "A Simple Microassay for Erythropoietin Based on $^{3}H$-thymidine Incorporation into Spleen Cells from Phenylhydrazine Treated Mice," Exp. Hematol., JI: 649–660 (1983), which is hereby incorporated by reference. For each assay, a single mouse was treated with an intraperitoneal injection of phenylhydrazine (60 mg/kg body weight) for 2 consecutive days to induce intravascular hemolysis. The resulting anemia stimulated extramedullary red blood cell hematopoiesis in the spleen. The mouse was sacrificed 3 days after the second phenylhydrazine injection. The spleen was removed by dissection, rinsed in sterile 0.01 M phosphate buffered saline (PBS, pH 7.4) at 37° C., and placed in a petri dish containing 5 ml Dulbecco's modified Eagle's medium supplemented with 10% (v/v) fetal bovine serum (Gibco BRL, Grand Island, N.Y.). Splenic cells were dissected from the capsule, and other consecutive tissues by extrusion through a wire mesh and aspiration through a 21-gauge needle. The cellular suspension was then transferred to a polypropylene tube. Residual pieces of tissue debris were allowed to settle over 5 minutes and the supernatant containing dispersed cells was transferred to a new tube. These spleen cells were then pelleted by centrifugation at 1,000 g, resuspended in 25 ml of culture medium, counted, and viability assessed by trypan blue dye exclusion. Analysis by light microscopy indicated that at least 90% of the cells were of the erythroid lineage. Aliquots of $4\times10^{6}$ cells were transferred to individual microcentrifuge tubes, pelleted, and resuspended in 1 ml of culture medium containing 11 different dilutions of either rcEPO or rhEPO.

Changes in DNA synthesis were used to compare rcEPO to rhEPO in terms of their abilities to stimulate the replication of splenic erythroid progenitor cells. Each erythropoietin dilution was evaluated in triplicate in a 96-well microtiter plate (Corning Science Products, Corning, N.Y.). The cells were plated at a density of $8\times10^5$ cells in 0.2 ml of culture medium. After 22 hours in culture, the cells were labeled for 2 hours with 0.2 μCi$^3$H-thymidiine (DuPont NEN, Boston, Mass.). Cells were harvested onto glass filter mats using a Skatron cell harvester (Flow Laboratories. McLean, Va.) and $^3$H-thymidinie decay events quantified in a liquid scintillation counter (Beckman, Palo Alto, Calif.). Medium without erythropoietin supplementation and medium conditioned by non-transfected CHO cells were used as negative controls.

The bioactivity of rcEPO was assessed in vivo by direct quantitation of circulating reticuloyctes in mice. Kawamura et al., "Simple in vivo Bioassay for Erythropoietin," Br. J. Haematol., 77:424–430 (1991). Normal adult C57BL/6J mice (The Jackson Laboratory, Bar Harbor, Me.) were injected subcutaneously for 3 successive days with either rcEPO or rhEPO at doses ranging from 0–20 units/mouse brought to a total volume of 200 μl with PBS. Commercial rhEPO (Epogen®, Amgen, Inc., Thousand Oaks, Calif.) was supplied at defined concentration of Internatinal Units per mililiter (Storring et al., "The International Standard for Recombinant DNA-derived Erythropoietin: Collaborative Study of four Recombinant DNA-derived Erythropoietins and Two Highly Purified Human Urinary Erythropoietins," J. Endrocinol., 134:459–484 (1992), which is hereby incorporated by reference). The amount of conditioned medium containing equivalent units of rcEPO was estimated by Western Blot analyses and in vitro bioactivity. Control mice received injections of culture medium conditioned by non-transfected CHO cells. One day after the third injection, an aliquot of peripheral blood was collected into EDTA-containing tubes. The percent of reticuloyctes in each blood sample was determined by flow cytometric analyses of 10,000 cells using the fluorescent dye thiazole orange (Retic-COUNT, Bectin-Dickinson, San Jose, Calif.). Lee et al., "Thiazole Orange: A New Dye for Reticulocyte Analysis," Cytometry, 7:508–517 (1986); Nobes et al., "Reticulocyte Counting Using Flow Cytometry," J. Clin. Pathol., 43:675–678 (1990), which are hereby incorporated by reference. Experimental protocols for both murine bioassays were reviewed and approved by the University's Institutional Animal Care and Use Committee.

Example 5

Statistical Analyses

For the in vivo bioassay, two-way analysis of variance was used to determine the effect of recombinant erythropoietin source (canine or human), the dose of erythropoietin used, and whether there was an intraction between source and dose. When the interaction was not significant, data were interpreted for the main effects. The least significant difference post hoc test was used to determine which doses differed from each other and control. A value of $p<0.05$ was considered significant.

Example 6

Results and Discussion

Canine EPO expression varied significantly between individual G418-resistant CHO cell clones co-transfected with pLEN-cEPO and pRSVneo. FIG. 19 illustrates comparative steady state levels of cEPO and EFTu mRNA in 100 individual clones. The clone used for subsequent rcEPO production was selected based on its high cEPO/EFTu mRNA ratio and excellent growth characteristics. Western analysis of rcEPO protein in conditioned tissue culture medium identified a broad band of approximately 30–34 kDa, which was roughly equivalent in size to commercial rhEPO (Epogen®, Amgen, Inc., Thousand Oaks, Calif., FIG. 3). Since erythropoietin is a glycosylated protein, enzymatic digestion of rcEPO and rhEPO with N-glycosidase (FIG. 3, lanes 4 and 6) removed the heterogeneic carbohydrate residues and resulted in a single 18.5 kDa broad, a size consistent to that predicted by the primary cDNA nucleotide sequence.

Figure 4A:
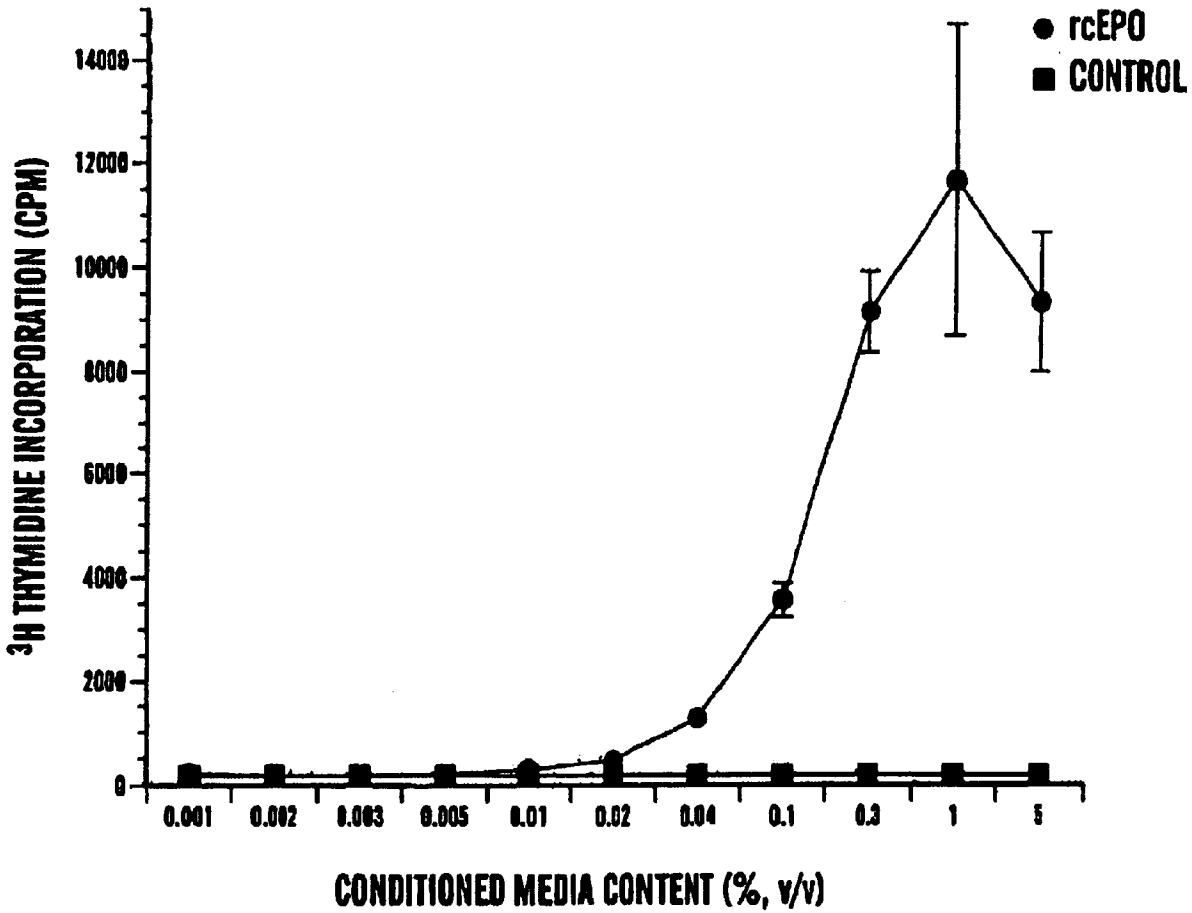
FIGS. 4A and 4B show the stimulation of erythroid progenitor cell division with rcEPO (FIG. 4A—conditioned medium from either control or rcEPO-expressing CHO cells) and rhEPO (FIG. 4B—rhEPO (Epogen®, Amgen, Thousand Oaks, Calif.). Extra-medullary hematopoiesis was stimulated in a mouse by phenylhydrazine-induced intravascular hemolysis. Erythroid progenitor cells were then isolated from the spleen and cultured for 22 hours in the presence of increasing concentrations of erythropoietin. The erythroid cell cultures were pulsed with 0.2 μCi $^{3}$H-thymidine during the last two hours of incubation. Cellular replication was evaluated by $^{3}$H-thymidine incorporation into newly synthesized DNA. Data points represent the mean (+/− standard deviation) of each concentration analyzed in triplicate.
Figure 4B:
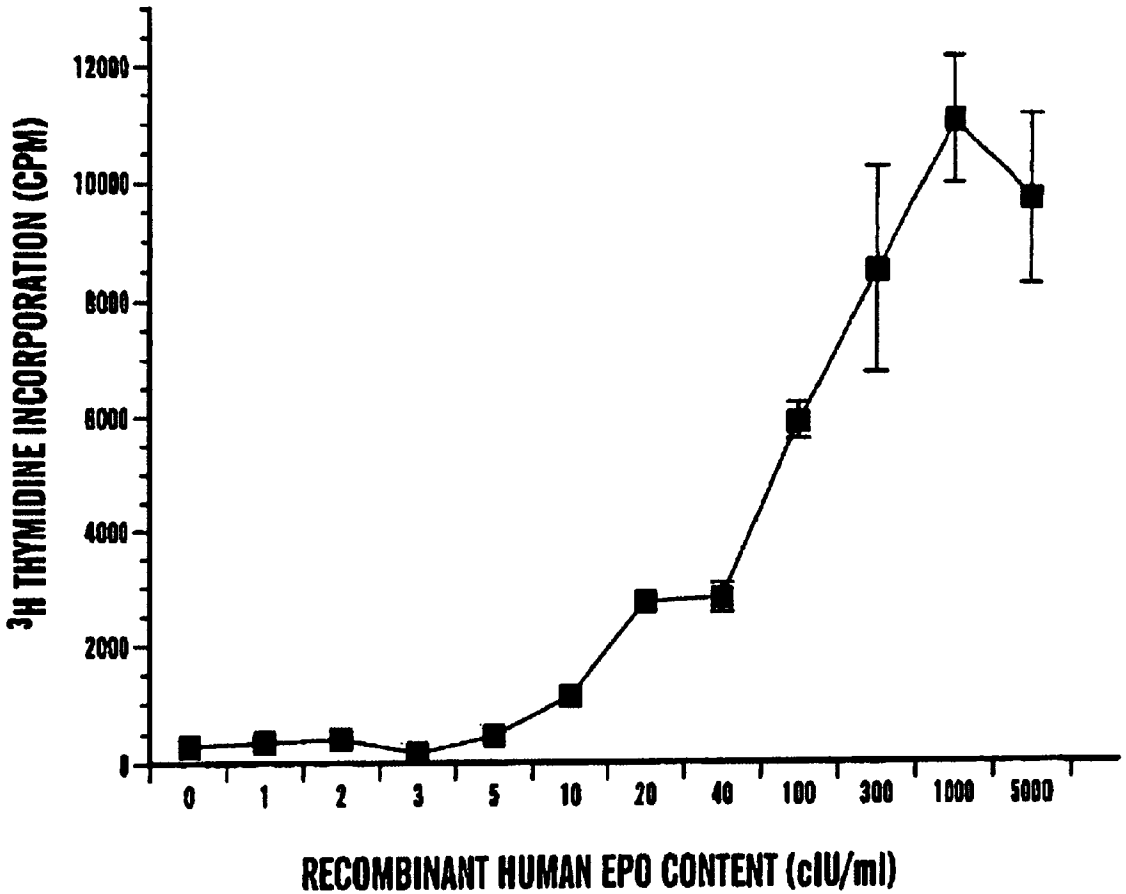
Figure 5:
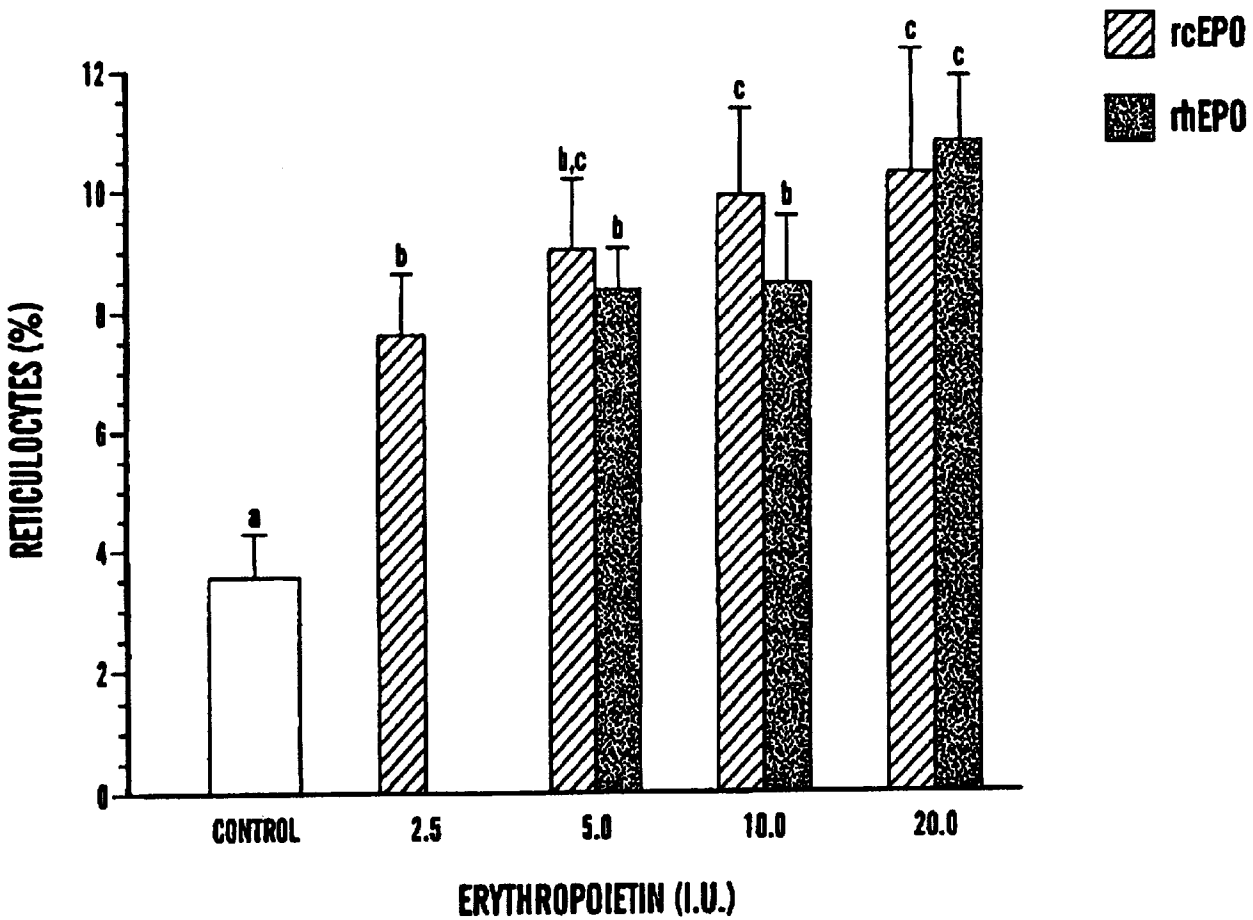
FIG. 5 shows the stimulation of reticulocytosis in mice with rcEPO and rhEPO. Normal C57BL/6J mice (approximately 8 weeks of age) were injected subcutaneously for three days in succession with rcEPO or rhEPO (Epogen®, Amgen, Thousand Oaks, Calif.) in a total volume of 200 μl PBS. Quantitative estimates of rcEPO units were based on in vitro bioactivity and Western Blot analyses. Control mice received injections of culture medium conditioned by nontransfected CHO cells. One day after the third injection, the mice were sacrificed and peripheral blood collected into EDTA-containing tubes. The percent of reticuloyctes in each blood sample was determined by flow cytometric analyses of 10,000 cells using the fluorescent dye thiazole orange (Retic-COUNT, Bectin-Dickinson). Each group represents the mean reticulocyte count (+/− standard deviation) of 4 mice. Different letters indicate $p<0.05$ between treatment groups.

Two assay systems were used to compare the bioactivity of rcEPO and rhEPO. In vitro, the replication of splenic erythroid progenitor cells was stimulated in a dose-dependent manner by increasing levels of rcEPO supplementation (FIG. 4A). No increase in 3H-thymidine incorporation was observed with culture medium conditioned by control CHO cells. The rcEPO stimulation exhibited an overall pattern of activity broadly parallel to commercial rhEPO (Eopgen®, Amgen, Inc., Thousand Oaks, Calif., FIG. 4B). Similar bioactivity results were obtained using an in vivo murine assay based on erythropoietin-induced stimulation with reticulocytosis. Untreated mice or mice injected with conditioned medium from control CHO cells had peripheral reticulocyte counts of approximately 3.5%. The counts increased significantly in a dose dependent fashion in response to both rhEPO and rcEPO (FIG. 5).

Erythropoietin deficiency is the most important cause for the nonregenerative anemia that develops during chronic or acute renal failure. It results from the loss of erythropoietin-producing cells in the kidney during renal disease progression. This is true for both humans and companion animals. Recombinant hEPO became commercially available in 1989 and has dramatically improved the ability to manage this problem in humans. Exogenous erythropoietin replacement rapidly restores red blood cells mass and hemoglobin concentrations to normal levels and helps resolve many of the clinical symptoms associated with end-staoe renal disease. Therapeutic failure of rhEPO in companion animals, estimated with an incidence between 20 and 50%, appears to result from interspecies variation in erythropoietin structure. Although biological activity of rhEPO is retained, the human protein is frequently recognized as foreign by the immune system. The concept of erythropoietin replacement is appropriate for companion animals, the problem is the immunogenicity of rhEPO. The pathogenesis and current treatment options for the anemia of chronic or acute renal failure in dogs and cats have been reviewed by Cowgill, "Medical Management of the Anemia of Chronic Renal Failure," In: Canine and Feline Nephrology and Urology, Osborne, et al., eds. Baltimore: William & Wilkins, 539–554 (1995), which is hereby incorporated by reference.

The present invention demonstrates the feasibility of developing species-specific recombinant erythropoietin preparations. PCR was used to amplify a canine erythropoietin cDNA fragment that was then used as a probe to isolate phage clones containing the erythropoietin gene from a canine genomic library. DNA sequence analysis demonstrated 85.5% nucleotide identity with human erythropoietin over the full coding region and predicts 81.3% identity at the amino acid level. Sequence analysis was carried out using the MacVector program with the default parameters. The 18.7% difference in primary amino acid sequence is consistent with rhEPO being potentially immunogenic in dogs.

Figure 2:
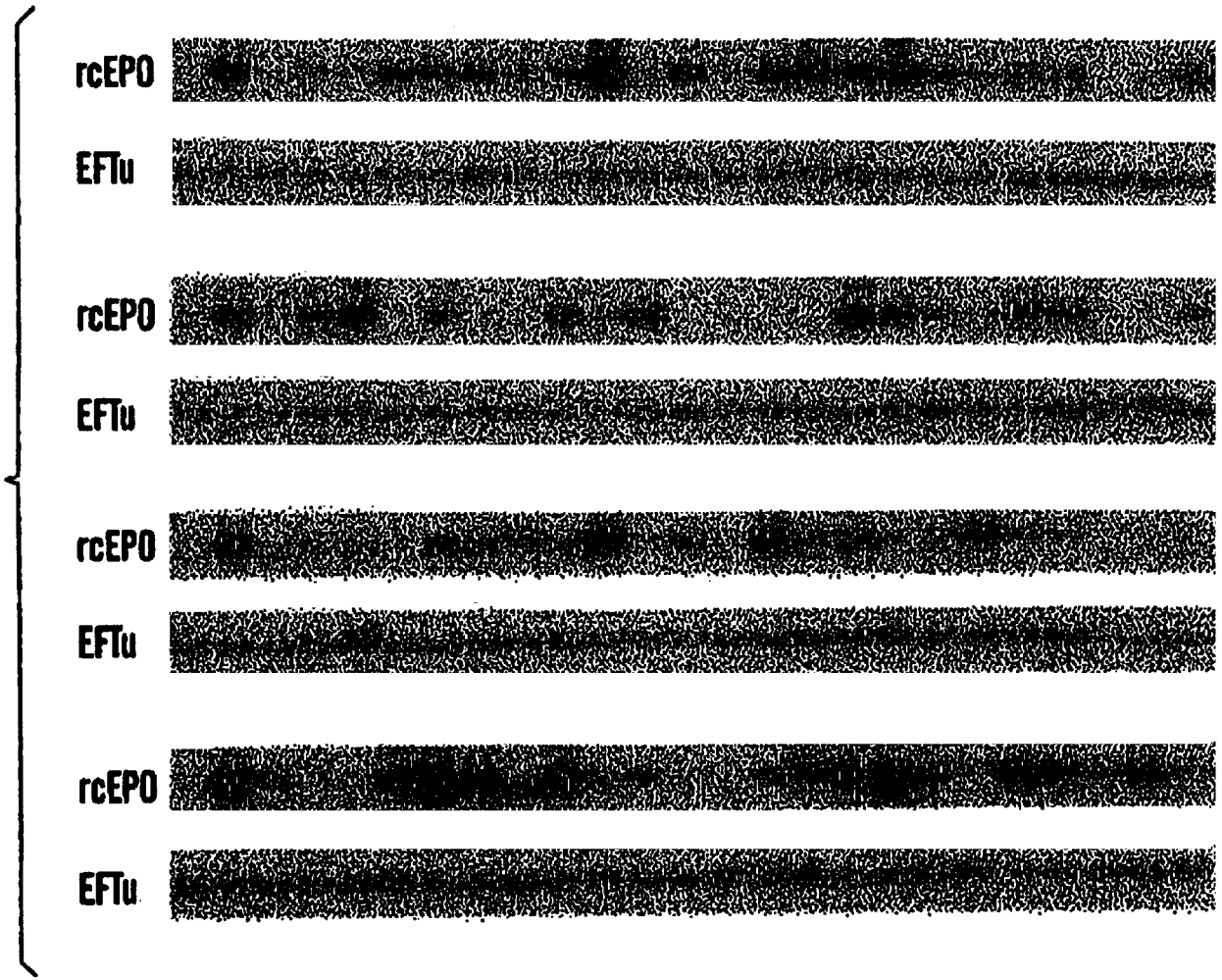
FIG. 2 shows a comparative analysis of steady state cEPO mRNA in chinese hamster ovary ("CHO") cell clones. Total RNA was isolated from 100 individual CHO cell clones by acid guanidinium thiocyaante-phenol-chloroform extraction followed by differential alcohol and salt precipitation. The RNA was resolved electrophoretically (5 μg/lane), transferred to a nylon membrane, and hydridized sequentially with $^{32}$P-labeled cDNA probes for canine erythropoietin and the housekeeping gene EFTu. Clones with high levels of cEPO expression were identified by phosphor image quantitation (Fujix Bio-imaging and MacBAS software, Fuji (Stamford, Conn.) of steady state cEPO mRNA levels normalized to the expression of EFTu.
Figure 3:
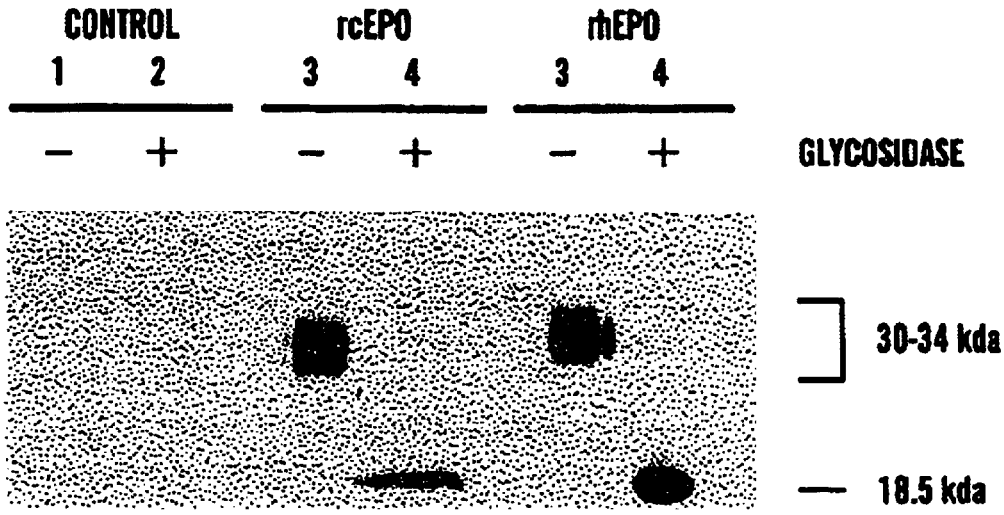
FIG. 3 shows a Western Blot analysis of rcEPO and rhEPO structure. Conditioned medium (30 μm) from a high rcEPO expressing CHO cell clone was compared to 15 units of rhEPO both without (−) or with (+) pretreatment with N-glycosidase (PNGase F, New England Biolabs, Beverly, Mass.). The samples were resolved electrophoretically under reducing conditions by SDS-PAGE and transferred to a nitrocellulose membrane. The membrane was then incubated with a primary antibody against erythropoictin and developed using a commercial enhanced chemiluminescence procedure (ECL Western Blotting detection system, Amersham, Arlington Heights, Ill.). Control samples were tissue culture medium (30 μl) conditioned by CHO cells that were not transfected with the pLEN-cEPO expression plasmid.

Individual CHO cell clones transfected with the pLEN-cEPO construct variety by more than 100 fold in levels of rcEPO expression (FIG. 2). This likely reflects differences in the site of integration and copy number of the transgene incorporated. The size and apparent total glycosylation of rcEPO was comparable to commercial rhEPO (FIG. 3). Importantly, the in vitro (FIG. 4) and in vivo (FIG. 5) biological activity profiles of rcEPO and rhEPO were similar in the two murine-based assays used in this study. Combined, these results predict that rcEPO will stimulate erythropoiesis in dogs suffering from anemia secondary to an absolute or relative deficiency of endogenous erythropoietin. Potential for an important therapeutic advance is based on the prediction that use of homologouserythropoietin preparations will avoid the serious problems of rhEPO's immunogenicity in companion animals.

Example 7

Purification of Recombinant Canine Ersythropoietin rcEPO conditioned serum free tissue culture medium was used for clinical trial and bioactivity assays. An estimate of the rcEPO concentration in different batches of conditioned medium was determined by Western blot analyses as illustrated in FIG. 3. For commercial use in companion animals, however, the rcEPO must be purified and concentrated. Published methods that have been used to purify human erythropoietin from the urine of sickel cell anemia patients should be applicable to the purification of rcEPO from conditioned tissue culture medium. Miyake et al., "Purification of Human Erythropoietin," J. Biol. Chem., 252:5558–5564 (1977); Krystal et al., "Purification of Human Erythropoietin to Homogeneity by a Rapid Five-Step Procedure." Blood, 67:71–79 (1986), which are hereby incorporated by reference. In fact, the process should be considerably easier since the starting concentration of rcEPO is orders of magnitude higher than the level of EPO in human urine and the CHO cells can now be cultured under completely serum free conditions.

In particular, the urine is filtered through a 0.45 gm membrane to remove cellular debris and other particulates. The filtrate is then applied to an ion exchange resin (CM Affi-Gel Blue, Pharmacia Biotech Inc., Piscataway, N.J.) pre-equilibrated with 0.15 M NaCl and 10 mM $NaPO^4$, pH 7.2. Bound proteins are eluted from the column with a steep salt gradient from 0.15 M to 1.15 M NaCl in the same buffer (rcEPO elutes in a broad peak at approximately 0.9 M NaCl). the elute is then concentrated by ultrafiltration (amicon Model 402, Lexington, Mass.) and dialyzed overnight against 20 mM Tris-HCl, 0.1% PEG 4000, pH 7.0. The second purification step involves chromatofocusing (PBE94 column-polybuffer exchanger, Pharmacia Biotech) with a pH gradient from 7.0 to 3.8 and back to 7.0. The pI of erythropoietin is reported to be approximately 3.5 and the protein remains bound to the column. It is then eluted with high salt (0.3 M NaCl in 20 mM Tris-HCl, pH 7.0) rather than lowering the pH of the eluent below erythropoietin's isoelectric point. The strategy of published methods diverge at this point. Krystal et al., "Purification of Human Erythropoietin to Homogeneity by a Rapid Five-Step Procedure," Blood, 67:71–79 (1986), which is hereby incorporated by reference, proceed with wheat germ lectin chromatography. The lectin, coupled to a Sepharose 6 MB macrobead support (Pharmacia Biotech), binds N-acetyl-β-D-glucosaininyl and sialic acid residues in the carbohydrate side chains in erythropoietin. Non-glycosylated proteins wash through the column. Bound rcEPO is then eluted with 10 M N-acetyl-D-glucosamine in PBS containing 0.02% Tween 20. In contrast, an earlier procedure (Miyake et al., "Purification of Human Erythropoietin." J. Biol. Chem., 252:5558–5564 (1977) which is hereby incorporated by reference) utilizes Sephadex G-100 (Pharmacia Biotech) gel filtration chromatography. After concentration by ultrafiltration, final purification steps employ reverse-phase HPLC using either n-propanol or acetronitrile gradients.

Example 8

Materials and Methods for Examples 9–10

Erythropoietin preparations. Methods used in the production of rcEPO have been described (MacLeod, et al., "Expression and Bioactivity of Recombinant Canine Erythropoietin," Am. J. Vet. Res., 59:1144–1148 (1998), which is hereby incorporated by reference). Briefly, the gene encoding cEPO was isolated from a genomic library, subcdonded into a eucaryotic expression vector, and transfected into Chinese hamster ovary (CHO) cells (ATCC CRL-9618). A single high rcEPO-expressing CHO clone was adapted for growth in defined serum-free medium[a]. Concentration of rcEPO in conditioned medium was estimated by use of immunoblot analyses and in vivo bioassasy (MacLeod, et al., "Expression and Bioactivity of Recombinant Canine Erythropoietin," Am. J. Vet. Res., 59:1144–1148 (1998), which is hereby incorporated by reference). For treatment of dogs, the concentration of rcEPO was normalized to 500 U/ml, using medium conditioned by nontransfected control CHO cells as a diluent and supplemented with 0.25% (wt/vol) canine albumin and 0.025% (wt/vol) human albumin[b]. The rhEPO was purchased at a concentration of 10,000 U/ml,[c] diluted to a concentration of 500 U/ml with medium conditioned by control CHO cells, and supplemented with canine and human albumin to final concentrations of 0.25 and 0.025%, respectively. The diluent administered to dogs during weeks −4 to 0 consisted of medium conditioned by control CHO cells and supplemented with canine and human albumin. The 3 preparations were sterilized by passage through 0.22 μm filters and stored frozen at −20 C om sterile vials until used.

Dogs. Thirteen sexually intact clinically normal Baegels (9 females, 4 ales) were studied for 28 weeks. Age of dogs was between 1.2 and 6.5 years (median 1.3 years), and body weight was between 10.9 and 17.7 kg (mean, 13.7 kg) For 2 weeks prior to the start of the study, dogs were acclimiated to environmental conditions and handling procedures. All dogs were housed in same-sex groups of 2 or 3 and fed commercial dry dog food, with water available ad libitum. Dogs were observed daily and cared for in a routine manner, including vaccination[d] at the onset of the steady against canine distemper and adenovirus type-2, coronavirus, parvovirus, and leptospiral infections. The study was approved by the Institutional Animal Care and Use Committee of Cornell University.

Dogs were randomly assigned to 2 groups; 1 group (dogs 1 to 6; 5 females, 1 male) received rhEPO, and the second group (dogs 7 to 13; 4 females, 3 males) received rcEPOc. Both groups received diluent, SC, 3 times a week for 4 weeks (weeks −4 to 0) before initiating EPO (100 U/kg) of body weight, SC 3 times/wk) treatment. This dosage of rhEPO has been used by others to successfully stimulate erythropoiesis in dogs (Giger, "Erythropoietin and its Clinical Use," Compend. Contin. Educ. Pract. Vet., 14:25–34 (1992); Cowgill, "Medical Management of the Anemia of Chronic Renal Failure," In: "Osborne Calif., Finco DR, eds. Canine and feline nephrology and urology. Baltimore: The Williams & Wilkins Co., 539–544 (1995), which are hereby incorporated by reference). All dogs received supplemental iron (ferrous sulfate,[e] 10 mg/kg, PO, daily or every other day) starting at the onset of EPO treatment.

During the steady, if Hct of any dog exceeded 65% for 2 consecutive weeks, the EPO dose was decreased to 100 U/kg once weekly to avoid clinical problems associated with polycythemia. If dogs were receiving EPO at a dosage of 100 U/kg 3 times, and a >10% decrease from the highest Hct determined after EPO treatment began was documented for 2 consecutive weeks, EPO administration was stopped because of suspicion of erythroid hypoplasia. If dogs receiving EPO at a dosage of 100 U/kg once weekly, and a >10% decrease from the highest Hct determined after EPO treatment began was documented for 2 consecutive weeks, EPO administration was restored to 100 U/kg 3 times weekly.

Laboratory assessments. Complete blood counts were performed monthly. Serum biochemical anlayses (sodium, potassium, chloride, total protein, albumin, globulin, BUN, creatine, glucose, calcium, phosphorus, total bilirubin, cholesterol, and iron concentrations, alkaline phosphatase, aspartate transaminase, alanine, transaminase, γ-glutamyltransferase, creatine kinase, and amylase activities, and unsaturated iron binding capacity) were done prior to initiating EPO treatment and at the end of the study, using automated procedures.[f] Total iron-binding capacity (TIBC) was determined by summation of serum iron concentration and unsaturated iron-binding capacity. Transferrin saturation was calculated as follows:

(serum iron concentration/TIBC)×100

Hematocrit (%) and RBC number ($10^6$ μl) were determined weekly, using automated procedures.[g] Reticulocyte count (%) was determined weekly from new methylene blue-stained blood smears examined by use of oil immersion light microscopy with the aid of a Miller's disk occuLar[h] in 2 dogs and by use of flow cytometry[i] in 11 dogs. Absolute reticulocyte count was calculated by multiplying the reticulocyte count (%) by the RBC count ($10^6$/μl).

Bone marrow cytologic examination. Bone marrow aspirates were collected from the wing of the ilium or proximal portion of the humerus as described (Relford, "The Steps in Performing a Bone Marrow Aspiration and Core Biopsy," Vet. Med., 86:670–688 (1991), which is hereby incorporated by reference), except that specimens were aspirated into a syringe containing 1 ml of citrate-phosphate-dextose solution. Bone marrow smears were prepared from spiculated portions of the specimen and stained with modified Weight-giemsa.[i] Myeloid-to-erythroid ratio (M:E) was determined from a 500 cell differential count. On the basis of the amount and intensity of stain updatek, iron stores were assessed on Prussian blue-tained bone marrow smears as absent, low, normal, or increased. Bone marrow aspiration was performed before treatment with EPO (week 0) and at weeks 4, 8, 16 and 24. For the aspiration procedure, dogs were sedated with oxymorphone hydrochloride (0.05 to 0.10 mg/kg, 1M) and midazolam (0.20 mg.kg, 1M).

Statistical analyses. The proportion of dogs developing from a 500 cell differential count. On the basis of the amount erythroid hypoplasia in the 2 groups was compared, using Fischer's exact test (Dawson-Saunders, et al., "Basic and Clinical Biostatistics," Norwal, Conn.: Appleton and Lange, 109–100, 114–116 (1994), which is hereby incorporated by reference). Hematologic and biochemical variables were compared before and after rcEPO or rhEPO treatment in each group, using the paired t-test (Dawson-Saunders, et al., "Basic and Clinical Biostatistics," Norwalk, Conn.: Appleton and Lange, 109–110, 114–116 (1994), which is hereby incorporated by reference). Differences in mean Hct, absolute reticulocyte count, leukocyte count, platelet number, and mean corpuscular volume (MCV) between rcEPO-treated dogs were evaluated at 4-, 8-, 192–16, 20-, and 24-week time points, using Student's t-test (Dawson-Saunders, eta l., "Basic and Clinical Biostatistics." Norwalk, Conn.: Appleton and Lange, 109–100, 114–116 (1994), which is hereby incorporated by reference). Values of P are reported with and without the bonferroni correction for multiple comparisons (Dawson-Saunders, et al., "Basic and Clinical Biostatistics," Norwalk, Conn.: Appleton and Lange, 109–100, 114–116 (1994), which is hereby incorporated by reference).

Example 9

Hct and Absolute Reticulocyte Count in Dogs during EPO Treatment

Figure 6B:
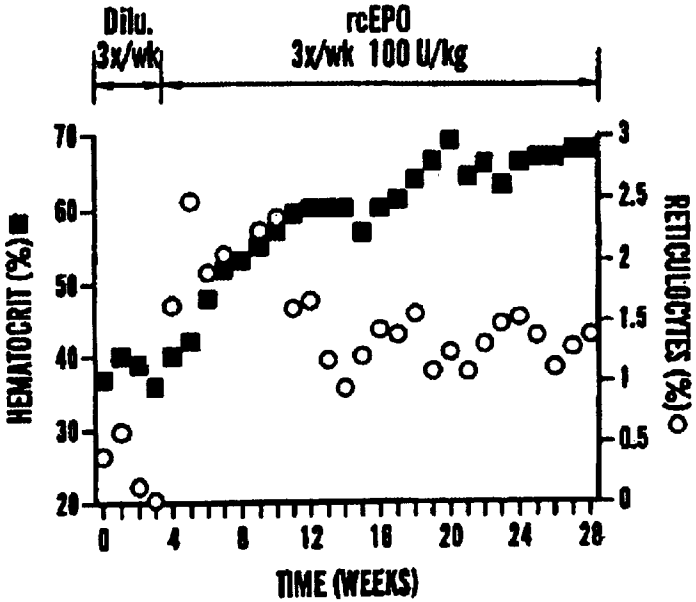
FIGS. 6A and 6B show the hematocrit and reticulocyte response to human or canine recombinant erythropoietin in normal Beagles. In the first four weeks, both dogs were treated with diluent. Starting with week four, either rhEPO (FIG. 6A) or rcEPO (FIG. 6B) was administered subcutaneously at a dose of 100 units/kg thrice weekly. Changes in weekly hematocrit (■) and reticulocyte (o) values are illustrated.
Figure 6A:
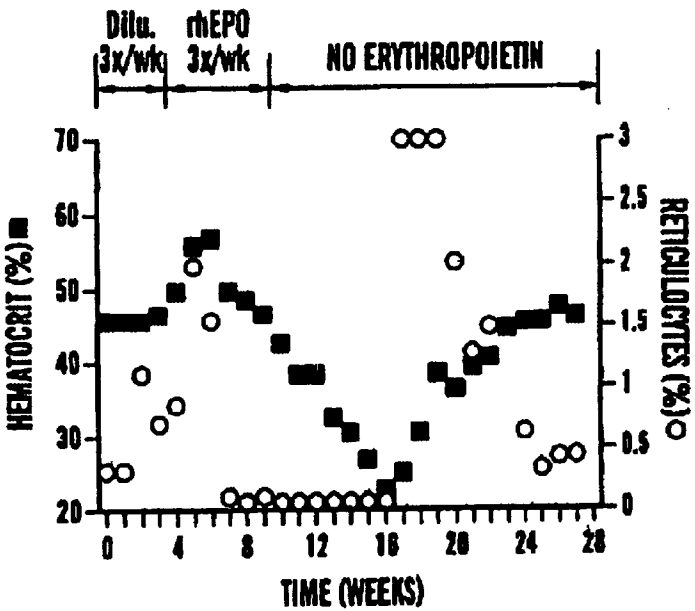
Figure 7B:
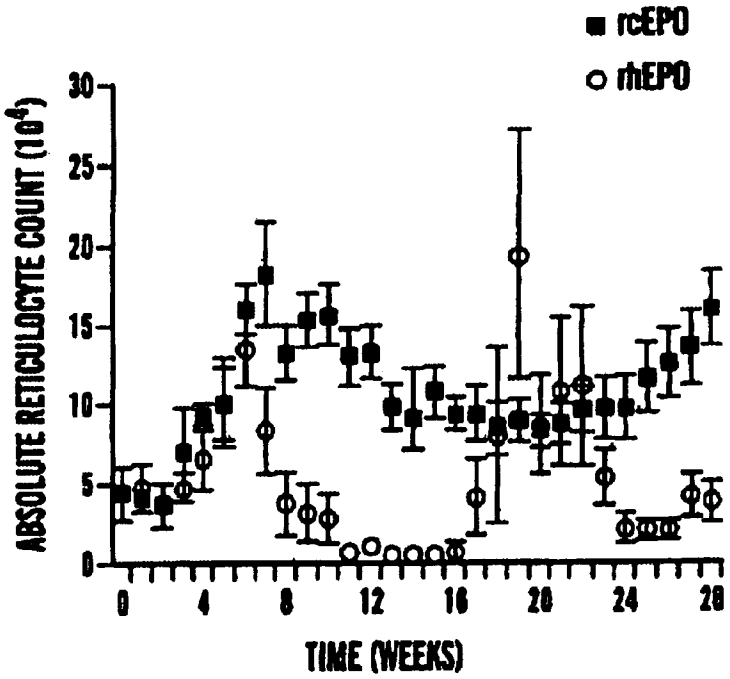
FIGS. 7A and 7B show pooled data illustrating hematocrit (FIG. 7A) and reticulocyte (FIG. 7B) response to human or canine recombinant erythropoietin in normal Beagles. During the first four weeks, dogs in both groups were treated with diluent. Starting with week four, either rcEPO (■, n=7) or rhEPO (o, n=6) was administered subcutaneously and thrice weekly at a dose of 100 units/kg. Changes in the weekly hematocrit and reticulocyte values are illustrated. Therapy was halted in all rhEPO-traeted dogs during the experimental period due to development of red cell aplasia. Administration frequency of rcEPO was reduced in some dogs due to hematocrit values that rose above 65%.
Figure 7A:
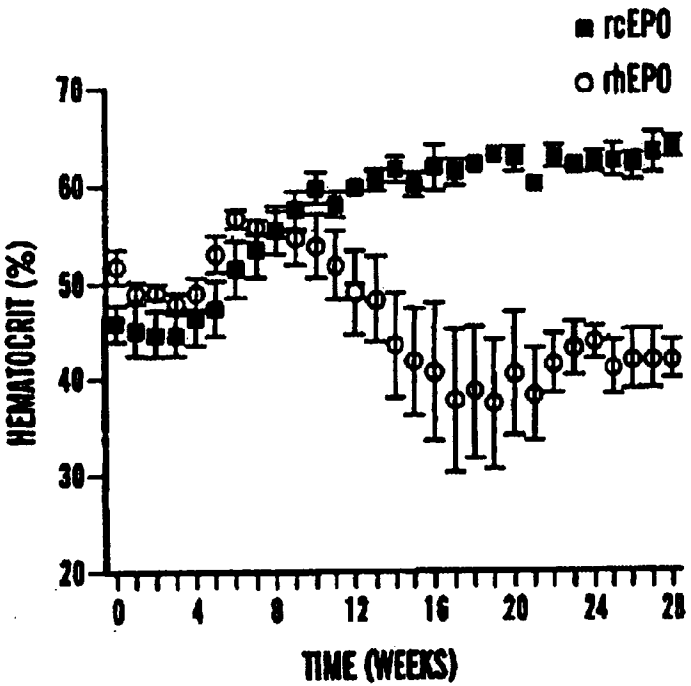

Weekly mean Hct and absolute reticulocyte count increased in both groups of dogs during the first 2 weeks of EPO treatment (FIG. 6). For dogs receiving rcEPO, mean Hct continued to increase and, after week 4, exceeded the reference range (39 to 57%) throughout the study. In contrast, mean Hct for dogs receiving rhEPO decreased after week 2 and, for weeks 13, 14, 15 and 17, was less than the reference range. (FIG. 13A). Mean Hct in rhEPO- and rcEPO-treated dogs was significantly ($P \leqq 0.05$) different for weeks 8 through 24. If a consecutive $P<0.0078$ cutoff is used because of multiple comparisons. Hct for the 2 groups were significantly different at weeks 20 and 24. Weekly mean absolute reticulocyte count peaked at 3 weeks of rcEPO treatment and exceeded the reference range (≦60,000 cells/μl) throughout the study (FIG. 13B). For rhEPO-treated dogs, mean absolute reticulocyte count peaked after 2 weeks, decreased to within the reference range for weeks 4 through 14; then, after rhEPO treatment had been discontinued in most dogs in this group, increased to >60,000 cells/μl for weeks 15 through 19. Mean absolute reticulocyte counts were significantly different between the 2 groups for weeks 4 through 12 ($P \leqq 0.008$) and week 24 $P \leqq 0.05$).

Example 10

Erythroid Hypoplasia in Dogs Receiving rhEPO

All dogs (95% confidence interval, 63 to 100%) receiving rhEPO developed erythroid hypoplasia, with M:E>15:1 (reference range, 0.75:1 to 2.5:1), by week 4 (n=4),8 (1), or 16 (1). In fact, 5 of these dogs had M:E≧49:1. With cessation of rhEPO treatment after diagnosis of erythroid hypoplasia, erythrocyte production recovered 5 to 11 weeks (median 7 weeks) later in 5 of the 6 dogs (dogs 1 to 5). Dog 6 died of presumed anaphylaxis while still manifesting erythroid hypoplasia.

Unexpectedly, dog 1 redeveloped erythroid hypoplasia at week 24, even though treatment with rhEPO was reinstituted. In contrast, none (95% confidence interval, 0 to 37%) of the 7 dogs receiving rcEPO developed erythroid hypoplasia during the study. In fact, during rcEPO treatment, all bone marrow specimens examined had erythroid hyperplasia, with M:E of <0.75:1, except for dog 11 at week 16, which had cytologically normal bone marrow (M:E= 0.96:1). However, that dog's rcEPO dosage had been reduced to 100 U/kg/wk 6 weeks earlier between Hct was >65%: with reinstitution of 3-times-weekly rcEPO treatment, erythroid hyperplasia (M:E=0.61:1) redeveloped. The proportion of dogs developing erythroid hyperplasia was significantly (P≦0.01) different between the 2 groups.

Monthly mean leukocyte count was within the reference range (7.5 to 19.9×$10^3$ cells/μl) throughout the study for dogs receiving rcEPO. However, the rhEPO-treated dogs had mean leukocyte count below the reference range for weeks 8 through 16. (FIG. 2A). Differential leukocyte count for weeks 8 through 16 in rhEPO-treated dogs indicated neutropenia. Mean leukocyte count in rhEPO-treated dogs was significantly (P≦0.008) different from that in rcEPO-treated dogs for weeks 8 through 24. Monthly mean platelet count for rcEPO- or rhEPO-treated dogs varied but was within the reference range (1790 to 510×$10^3$ cells/μl) throughout the study (FIG. 2B). At week 16, mean platelet counts for the 2 groups differed significantly (P=0.05).

Monthly mean MCV decreased in both groups of dogs between weeks 4 and 12 (FIG. 2C). For dogs receiving rcEPO, means MCV continued to decrease and, for weeks 16 through 24, was less than the reference range (64 to 73 ff). In contrast, mean MCV in rhEPO-treated dogs increased for weeks 16 through 24 after cessation of rhEPO treatment. Mean corpuscular volume for the 2 groups differed significantly (P–0.004) at week 24. Mean corpuscular hemoglobulin concentration (MCHC) for both groups of dogs remained within the reference range (31 to 37 g/dl).

Bone marrow iron stores were normal to increased in all dogs initially. However, 6 of 7 rcEPO-treated dogs and 2 of 6 rhEPO-treated dogs had decreased marrow iron stores during periods of erythroid hyperplasia. Mean serum biochemical variable were within reference ranges at weeks 0 and 24 for rhEPO- and rcEPO-treated dogs (Table 1). However, in each group, specific significant differences was identified.

TABLE 1

Mean ± SEM values determined for serum biochemical variables at weeks 0 and 24 in clinically normal Beagles treated with recombinant human erythropoietin (rhEPO) or recombinant canine erythropoietin (rcEPO)[x]

| | | rhEPO | | rcEPO | |
|---|---|---|---|---|---|
| Variable | Reference range | Week 0 (n = 6) | Week 24 (n = 5) | Week 0 (n = 7) | Week 24 (n = 7) |
| Sodium (mEq/L) | 141-156 | 146 ± 2 | 147 ± 4 | 146 ± 2 | 147 ± 4 |
| Potassium (mEq/L) | 3.8-5.5 | 4.6 ± 0.2 | 4.5 ± 0.2 | 4.6 ± 0.4 | 5.3 ± 0.5[a] |
| Chloride (mEq/L) | 109-124 | 112 ± 1 | 111 ± 4 | 110 ± 3 | 109 ± 2 |
| BUN (mg/dl) | 8-30 | 16 ± 8 | 16 ± 4 | 25 ± 11 | 13 ± 4[a] |
| Cr (mg/dl) | 0.5-1.4 | 0.5 ± 0.1 | 0.5 ± 0.1 | 0.5 ± 0.1 | 0.6 ± 0.1[a] |
| Calcium (mg/dl) | 7.2-12.8 | 9.8 ± 0.3 | 10.1 ± 0.2[a] | 10.0 ± 0.3 | 10.4 ± 0.7 |
| Phosphorus (mg/dl) | 2.3-6.5 | 4.3 ± 0.4 | 4.0 ± 0.5[a] | 4.4 ± 1.1 | 4.7 ± 0.9 |
| TP (g/dl) | 5.6-7.9 | 6.6 ± 0.6 | 6.6 ± 0.3 | 6.6 ± 0.5 | 7.1 ± 0.3 |
| Albumin (g/dl) | 3.0-4.5 | 3.8 ± 0.2 | 3.8 ± 0.3 | 3.7 ± 0.2 | 3.7 ± 0.3 |
| Globulin (g/dl) | 1.8-4.2 | 2.8 ± 0.6 | 2.8 ± 0.5 | 2.9 ± 0.5 | 3.5 ± 0.5[a] |
| Glucose (mg/dl) | 60-120 | 89 ± 12 | 92 ± 5 | 94 ± 20 | 74 ± 15[a] |
| ALT (U/L) | 13-79 | 47 ± 19 | 35 ± 14 | 46 ± 8 | 48 ± 15 |
| AST (U/L) | 13-52 | 24 ± 11 | 17 ± 5 | 21 ± 4 | 20 ± 4 |
| ALP (U/L) | 12-122 | 52 ± 21 | 55 ± 18 | 55 ± 25 | 70 ± 35 |
| GGT (U/L) | 0-10 | 8 ± 2 | 5 ± 2[b] | 6 ± 1 | 5 ± 1 |
| T Bili (mg/dl) | 0.1-0.4 | 0.2 ± 0.1 | 0.1 ± 0.0 | 0.2 ± 0.1 | 0.2 ± 0.0 |
| Amylase (U/L) | 454-1,380 | 754 ± 100 | 845 ± 156[a] | 792 ± 229 | 883 ± 247[a,b] |
| Chol (mg/dl) | 124-335 | 139 ± 18 | 189 ± 39 | 189 ± 93 | 254 ± 141[a] |
| CK (U/L) | 58-241 | 219 ± 282 | 62 ± 17[a] | 99 ± 16 | 84 ± 23 |
| Iron (μg/dl) | 46-241 | 134 ± 23 | 148 ± 54 | 147 ± 31 | 159 ± 29 |
| TIBC (μg/dl) | 235-495 | 363 ± 44 | 458 ± 92 | 432 ± 118 | 470 ± 92 |
| % SAT (%) | 17-69 | 37 ± 4 | 33 ± 11 | 35 ± 5 | 35 ± 9 |

[x]Starting at week 0, rhEPO or rcEPO was administered SC 3 times weekly at a dose of 100 U/kg of body weight. Frequency of erythropoietin administration was reduced in 4 rcEPO- and 1 rhEPO-treated dogs because Hct increased to >65%. Treatment was discontinued in all rhEPO-treated dogs no later than week 19 because of development of erythroid hypoplasia. One rhEPO-treated dog died at week 15; definitive cause of death was not determined.

[a]Significant (P < 0.05) difference between weeks 0 and 24 without adjustment for multiple comparisons.

[b]Significant (P < 0.002) difference between weeks 0 and 24 with adjustment for 22 multiple comparisons.

Cr = creatinine. TP = total protein. ALT = alanine transaminase. AST = aspartate transaminase. ALP = alkaline phosphatase. GGT = γ-glutamyltransferase. T Bili = total bilirubin. Chol = cholesterol. CK = creatine kinase. TIBC = total iron-binding capacity. % SAT = percentage of transferrin saturation.

Other than changes in hematologic variables, the clinical status of each Beagle remained unchanged, with the exception of dogs 5, 6, 7, and 10. During the period of diluent administration, dogs 5 and 10 developed lethargy and fever of 1 days duration. Dog 5 was given an antibiotic (amoxicillin, 20 mg/kg, PO, q 12 h) for 5 days, but antibiotics were not given to dog 10, because the clinical signs of disease were less severe. Both dogs recovered without complications. Dog 7 treated with rcEPO developed bacterial conjunctivities of the right eye that required treatment with topically applied antibiotic ophthalmic ointment for the remainder of the study. After 15 weeks of study (4 weeks of diluent, 7 weeks of rhEPO, and 4 weeks after rhEPO treatment was discontinued), dog 7 died. Necropsy findings included acute diffuse severe pulmonary congestion and edema without histologic evidence of cardiac lesions, suggestive of anaphylaxis. The precipitating cause of death was not determined.

Example 11

Recombinant cEPO Rescues a Dog From rhEOP-Induced Red Cell Aplisia

Figure 8:
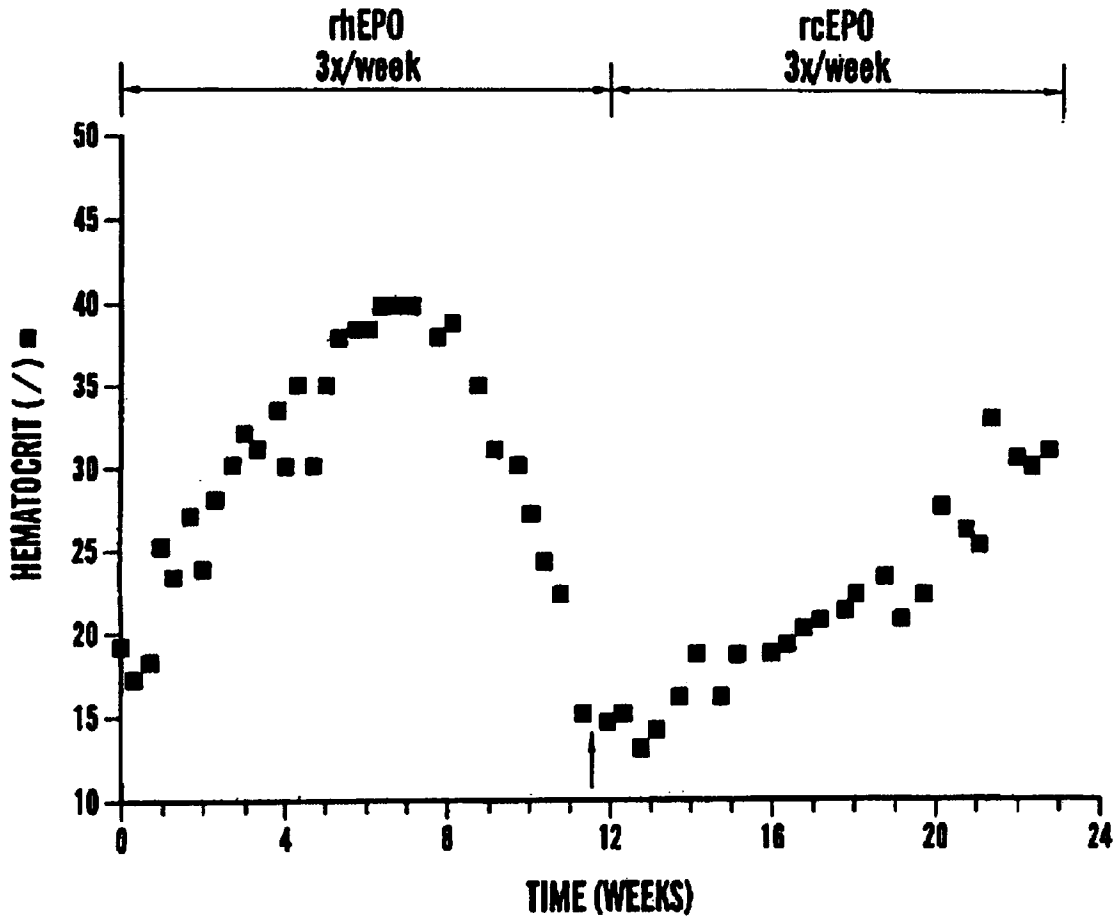
FIG. 8 demonstrates that recombinant cEPO rescues a dog from rhEPO-Induced red cell aplasia. Hematocrit is plotted over time. For approximately 12 weeks rhEPO was administered to the dog three times per week, followed by 12 weeks of administrationn of rcEPO, again at three times per week.

A dog with nonregenerative anemia secondary to chronic renal failure was treated with rhEPO (100 units/kg, three times a week)(See FIG. 8). The hematocrit rose for the first 6 weeks of therapy due to rhEPO stimulation of erythropoiesis. At approximately week 6 of therapy, the dog developed antibodies to rhEPO, blocking biological activity and inducing red cell plasia. From weeks 7 through 11, the hematocrit fell despite continued rhEPO therapy. At week 11, the hematocrit had dropped below 15% and a blood transfusion was given (arrow). Starting at week 12, therapy was changed to rcEPO. Recombinant cEPO (00 units/kg, three times a week) restored red blood cell production, initially stopped a further hematocrit decline and then stimulating a rise of hematocrit back towards normal levels.

Results of this study indicate that rcEPO stimulates erythrocyte production in clinically normal Baegels's during 24 weeks of treatment without the adverse effect of erythroid hypoplasia that was encountered during treatment of Beagles with rhEPO. Development of erythroid hypoplasia in rhEPO-treated dogs has been reported to coincide with appearance of antibodies against rhEPO (Cowgill, "Erythropoietin: Its Use in the Treatment of Chronic Renal Failure in Dogs and Cats," in Proceedings Annu. Waltham/OSU Sump Treat Small Anim. Dis., 15:65–71 (1991), which is hereby incorporated by reference). Seemingly, these antibodies are elicited because of an 18.7% difference in primary amino acid sequence between rhEPO and cEPO, rendering rhEPO potentially immunogenic in dogs (MacLeod, et al., "Expression and Bioactivity of Recombinant Canine Erythropoietin," Am. J. Vet. Res. 59:1144–1148 (1999), which is hereby incorporated by reference). In addition to blocking the efficacy of rhEPO, serocovnersion may result in cross-neutralization of endoenous cEPO, resulting in erythroid hypoplasia. Cowgill, "Erythropoietin: Its Use in the Treatment of Chronic Renal Failure in Dogs and Cats," in Proceedings Annu. Waltham/OSU Symp Treat Small Anim. Dis., 15:65–71 (1991); Giger, "Erythropoietin and Its Clinical Use." Compend. contin. Educ. Pract. Vet., 14:25–34 (1992); Cowgill, et al., "Use of Recombinant Human Erythropoetin For Management of Anemia in Dots and Cats With Renal Failure," J. Am. Vet. Med. Assoc., 212:521–528 (1998), which are herein incorporated by reference). In rats, mice, and rabbits, monoclonal antibodies to rhEPO interfere with biological activity of rhEPO and endogenous EPO (Goto, et al., "Characterization and Use of Monoclonal Antibodies directed Against Human Erythropoietin That Recognize Different Antigenic Determinants, Blood, 74:1415–1423 (1989), which is hereby incorporated by reference). Erythroid hypoplasia and anemia have also been reported after administration of rhEPO to cats (Cowgill, "Erythropoietin: Its Use in the Treatment of Chronic Renal Failure in Dogs and Cats," in Proceedings Annu. Waltham/OSU Symp Treat Small Anim. Dis., 15:65–71 (1991); Cowgill, et al., "Use of Recombinant Human Erythropoietin For Management of Anemia in Dogs and Cats With Renal Failure," J. Am. Vet. Med. Assoc., 212:512–528 (1998), which are hereby incorporated by reference) and horses (Woods, et al., "Nonregenerative Anemia Associated With Administration of Recombinant Human Erythropoietin to a Thoroughbred Racehorse," Equine Vet. J., 29:326–328 (1997); Piercy, et al., "Erythroid Hypoplasia and Anemia Following Administration of Recombinant human Erythropoietin to Two Horse," J. Am. Vet. Med. Assoc., 212:224–247 (1997), which are herein incorporated by reference). Data on the incidence of rhEPO-induced antibodies and erythroid hypoplasia in dogs are variable. In a study using dosages of rhEPO comparable to those used in this study, 3 of 16 clinically normal dogs developed antibodies to rhEPO associated with progressive anemia.[k] In another report (Bader, "Stimulation of Bone Marrow by Administration of Excessive Doses of Recombinant Human Erythropoietin," Pathol. Res. Pract., 188:676–679 (1992), which is hereby incorporated by reference) in which rhEPO was administered IV to 15 Beagles at extremely high dosages (100, 500, or 3,000 U/kg/d for 3 months), antibody production was not detected except in dogs in the highest dosage group. In uremic does receiving rhEPO at dosages greater than those used in this study, frequency of erythroid hypoplasia development approached 50% (Cowgill, Erythropoietin: Its Use in the Treatment of Chronic Renal Failure in Dogs and Cats," in Proceeding's, Annu. Waltham/OSU Symp. Treat Small Anim. Dis., 15:65–71 (1991), which is hereby incorporated by reference). The higher frequency (100%, 95% confidence interval, 63 to 100%) of erythroid hypoplasia encountered in the rhEPO-treated clinically normal dogs of our study may reflect a breed or familial predisposition to immunogenicity problems in our Beagle colony or a chance observation.

The time of erythroid hypoplasia in rhEPO-treated uremic dogs has been reported to be as early as 4 weeks after initiation of treatment, but typically, it is between 10 and 13 weeks (Cowgill, "Erythropoietin: Its Use in the Treatment of Chronic Renal Failure in Dogs and Cats," Proceedings, Annu. Waltham/OSU Symp. Treat Small Anim. Dis., 15:65–71 (1991), which is hereby incorporated by reference). In the rhEPO-treated clinically normal dogs of our study, bone marrow erythroid hypoplasia accompanied by decreasing Hct and absolute reticulocyte count was evident at 4 weeks in 4 of 6 dogs; the other 2 dogs developed erythroid hypoplasia by 8 and 16 weeks, respectively.

Recovery from rhEPO-induced erythroid hypoplasia after discontinuation of the dog has been described in dogs with chronic renal failure, but the rapidity and extent of recovery are variable depending in part on the diseased kidney's ability to produce adequate amounts of EPO (Cowgill, "Erythropoietin: Its Use in the Treatment of Chronic Renal Failure in Dogs and Cats," in Proceedings, Annu. Waltham/OSU Symp. Treat Small Anim. Dis, 15:65–71 (1991); Giger, "Erythropoietin and Its Clinical use," Compend. Contin. Educ. Pract. Vet., 14:25–34 (1992); Cowgill, "Clinical Experience and Use of Recombinant Human Erythropoietin in Uremic Dogs and Cats," in Proceedings, ACIVM Forum, 9:147–149 (1991), which are hereby incorporated by reference). In the clinically normal dogs of this study, erythrocyte production recovered 5 to 11 weeks (median, 7 weeks) after cessation of rhEPO treatment. However, after recovery, dog 1 redeveloped erythroid hypoplasia even through rhEPO treatment was not reinstituted. It is interesting to speculate whether anemnestic production of antibodies to rhEPO stimulated by the increase in endogenous. EPO may have resulted in recurrence of erythroid hypoplasia.

Treatment with rhEPO and rcEPO initially stimulated erythrocyte production, as evidenced by increasing mean Hct and absolute reticulocyte count during the first 2 to 3 weeks (FIG. 6). However, with the pressurized development of antibodies against rhEPO and resulting erythroid hypoplasia, mean absolute reciulatocyte count precipitously decreased, and mean Hct gradually decreased in rhEPO-treated dogs. A rebound increase in mean absolute reticulocyte count around week 16 significant recovery from erythroid hypoplasia in most dogs once rhEPO treatment was discontinued (FIG. 6B). In contrast, mean Hct for rcEPO-treated dogs continued to increase and, after week 4, exceeded the reference range (39 to 57%). In fact, 4 of 7 rcEPO-treated dogs required a reduction in the frequency of EPO treatment (from 3 times weekly to once weekly) because Hct exceeded 65%. Mean absolute reticulocyte count of >60,000 cells/μl and bone marrow cytologic findings of sustained erythroid hyperplasia during rcEPO treatment indicated continued stimulated erythropoiesis.

In conclusion, the collective data from this study indicate that rcEPO stimulates erythrocyte production in clinically normal Beagles during a 24-week treatment period without the adverse effect of erythroid hypoplasia commonly encountered in rhEPO-treated dogs. Recombinant cEPO appears to represent an improved option, compared with rhEPO, for treatment of absolute or relative EPO deficiency in dogs.

Although the invention has been described in detail for the purpose of illustration, it is understood that such detail is solely for that purpose and variations can be made by those skilled in the art without departing from the spirit and scope of the invention which is defined by the following claims.

SEQUENCE LISTING

<160> NUMBER OF SEQ ID NOS: 5

<210> SEQ ID NO 1
<211> LENGTH: 4491
<212> TYPE: DNA
<213> ORGANISM: Canis familiaris
<220> FEATURE:
<221> NAME/KEY: unsure
<222> LOCATION: (4372)
<223> OTHER INFORMATION: N at position 4372 is A, C, G, or T

<400> SEQUENCE: 1 tctagaacaa gtactgggat tgcgagaagg aaggcaactt gcctctgccc gcaccttccc 60 ggcttccaag gctagttgcc ccgcaggcac caggcaccgg cgctcccagc tcgatccccc 120 gcccaggact gggacgcacc cctccccccg gggggagggg ggcgggagcc tcggggtccc 180 cggcctttcc cagaatggca cccctcccgc gggtgcgcac ccagccgcgc ctcccacaac 240 ccggggtcag actggcggac ccgcgtcccg ctccgcgcct gctgccgcgc ctgctgccgc 300 tctgctcccg ccccggcgag cccccgaccc aggcgtcctg ccccggtctg acccctctgg 360 cccttacctc tggcgacccc tcacgcacac agcctgcccc ccacccccac acacgcacgc 420 acacatgctg ataacagccc cgaccccccgg ccgagccgca gtccccgggc caaccccggc 480 cggtcgccgc gcgcctgtcc tcgcggaccc tggccgagag ccctgcgctc gctctgcgcg 540 accccggctc ggcggcccct ggacggtggc cccctccttc ggaccgtggg gccggccctg 600 ccccgccgcg cttcccggga tgagggctcc cggcgagggc gccggcggag cccctggtcg 660 ctgagcggcc gacggaggcg cggagatggg ggcgtgcggt gagtactcgc cggccggagg 720 agcccccgcc cgctcgggcc cctgtttgag caagaattta ccgctggggc cccgaggtgg 780 ctgggttcaa ggaccgacga cttgccaagg accccggaag ggcaaggggg gtggggcagc 840 ccccacgtgc cggcagggct tagggagccc ctaggaaagg tgaaatctga cctggacacg 900 gggatgcggt ttgggggttc agggagaaga ggggctgcca cgtgcgtggg gagaaggctg 960 atacctgggt cttggagcaa tcaccgggat ctgccagagg ggaagcctca gtcacgccgg 1020 gattgaagtt tggccgggag aagtggatgc cggtagtttg gggggtgggg tgtgcgcgca 1080 gcagcggccg gattgaatga aggcagggga ggcagaacct gaacgctggg aaggtggggg 1140 tcgggcgcga ctagttgggg gcagaggagc gggatgtgtg aacctgcccc tccaaaccca 1200 cacagtcagc ctggcactct tttccagaat gtcctgccct gttccttttg ctgtctttgc 1260 tgctgcttcc tctgggcctc ccagtcctgg gcgcccccccc tcgcctcatt tgtgacagcc 1320 gggtcctgga gagatacatc ctggaggcca gggaggccga aaatgtcacg gtgagggtcc 1380 cacctcagga cattctcagt agtccagggg tgtcctccaa gatctgggaa cctgagcccc 1440

-continued

```
ttcgttcaga gatggagatg ggaagccaga gccctcagga aaaatgataa aagtggtagc   1500
ccctcaatgc atgcctggaa gctagatgag gggcaaaggt ggagggagct cttggggagc   1560
ctgacacccc cttccccccg acctggggtc atgcatttca gatgggctgt gctcaaggct   1620
gcagcttcag tgagaatatc accgtcccag acaccaaggt taatttctat acctggaaga   1680
ggatggatgt gagtttattt ttcccctcta cttggacagt cttgttttgc ttacctgatg   1740
gggtgggagg gagtaccata gaagaagctg agggctgaat gcaatatgtt tactcatttg   1800
ttctttgttc attcattaat tcattcattc aatgaaactg attccaagcc ttcattttgc   1860
tcagcttggt gcttggggct gctgagaggg aggggctggc ctgggccgct gactataagt   1920
cgccattccc tttaggttgg gcagcaggcc ttggaagtct ggcagggcct ggcactgctc   1980
tcagaagcca tcctgcgggg tcaggccctg ttggccaacg cctcccagcc atctgagact   2040
ccgcagctgc atgtggacaa agccgtcagc agcctgcgca gcctcacctc tctgcttcgg   2100
gcgctgggag cccaggtggg tagaagcctc ccttgcactt ctgctccaag ggccctgcca   2160
agaaatactg agaccccact ggacctcctc atcccccctc caattctgtc ctccatccca   2220
tctcccacca gggtcctggg cacttcggta accttctctt ctctccttgt cagaaggagg   2280
ccatgtccct tccagaggaa gcctctcctg ctccactccg aacattcact gttgatactt   2340
tgtgcaaact tttccgaatc tactccaatt tcctccgtgg aaagctgaca ctgtacacag   2400
gggaggcctg cagaagagga gacaggtgac caggtgctcc caccccaggc acatccacca   2460
cctcactcac taccactgcc tgggccacgc ctctgcacca ccactcctga cccctgtcca   2520
ggggtgatct gctcagcacc agcctgtccc ttggacactc cacggccagt ggtgatatct   2580
caagggccag aggaactgtc cagagctcaa atcagatcta aggatgtcac agtgccagcc   2640
tgaggcccga agcaggagga attcggagga aatcagctca aacttgggga cagagccttg   2700
ctcgggagac tcacctcggt gccctgccga acagtgatgc caggacaagc tggagggcaa   2760
ttgccgattt tttgcaccta tcagggagag acaggagagg ctagagaatc taggtggcaa   2820
gccataaatt ctctaggtct cgtgggtctc ctatgacagc aagagcccac tggcaaaggg   2880
tggtgggagc catggagatg ggataggggc tggcccctgg ctctcattgg gtccaagttt   2940
tgtgtatttt tcaatctcat tggcagaaac tgaaaccaca acatggctct tgacttttct   3000
gttttccctg ggatcctcct acttccctgg ccctgctccg gccctggcag caggccacag   3060
tcctggaaaa ctagaggtgg agggggtcgg ccctacgtgc tgcctctcat ggtctatctg   3120
acctcttgac cccactgggt ctgaggccac aagctctgcc cacgctggtc aataaggtgg   3180
ttctattcaa ggctgttcct cagtaggcag ttggcaaccc tctgtagtga gctacagctg   3240
ccatcaagga aacaggagcc aggaggaaga gcccctttgg gggctggtgg gagttcccag   3300
tcctggaccc tggaccctta ttatttctca cttctccata gtgcttttga ctaaagccac   3360
attcccacat cagcctttgc cacctctaaa tccagctgac ccttttcctt gcctgaggat   3420
ggtcaaggca aggaaatgct ctaccccaaa acttgcagaa ggagccacgt tccccaaaag   3480
cggtctcact gagcactcac tctgtgccca gggctattct aggtggttca cttacatgac   3540
attttattcc ttgcacagcc tgatgagaaa gtttccactg tcattcccag atgagaagta   3600
aactgcccaa agccaagaca acaggaatcc ccaatggccc cagctcttat cccttccctc   3660
ttcagcttat tcttccacat aacccctacc tgctccctgc tcccctggga tgggagacac   3720
agaacagact aactcagctc ccgctctcca tccctactaa taattttacc cagtactcca   3780
```

-continued

```
acattccact tcaaattcct tcccagaggg atgccttggt ggctcagtgg tagagtgtct   3840

gcctttgctc aggtcgtgat ccccaggtcc agagattgag tcctgcatca ggctccctgc   3900

agagagccca atcctgccat tatcatatgt gtggggatca gcctttctgc tcatatcaca   3960

aaacttagag aagtcagcct gcatccctga aaatatcaaa agaaaaagaa tttttgcaat   4020

ctgcaggagg acaaatgatg ggtcggttgg gggattggat ggtatgtgct aaatatatgt   4080

gtgtgtgctg gggggccgtg ccaagcgtgg tgggaggaat caaaggagag gtggacccaa   4140

aggagaattc ccccctcctc ccctgcctgg ccaactcagt tcctagggta tagtgccctc   4200

ttcaggcccc actggaaaat gttagagaaa tacacaagtc aaagagccct taggtctctg   4260

attattcttt gcacatttca ataaaaattt gtattacagt ttccacagat ggcatctggt   4320

tcttgcccca ctgctgtgaa acagtaaggg aggaatctgt ctctctcgct gncaaaatcg   4380

aagctaagag aggtgtccaa ggcatgcagc taataatggt agctaggacc tgaacacaag   4440

gtttaggaat cgtaacctcc aagcccatct tagcctgatg tgtcatctag a            4491
```

<210> SEQ ID NO 2
<211> LENGTH: 579
<212> TYPE: DNA
<213> ORGANISM: Canis familiaris

<400> SEQUENCE: 2

```
atgggggcgt gcgaatgtcc tgccctgttc cttttgctgt ctttgctgct gcttcctctg     60

ggcctcccag tcctgggcgc ccccccctcgc ctcatttgtg acagccgggt cctggagaga    120

tacatcctgg aggccaggga ggccgaaaat gtcacgatgg gctgtgctca aggctgcagc    180

ttcagtgaga atatcaccgt cccagacacc aaggttaatt tctatacctg gaagaggatg    240

gatgttgggc agcaggcctt ggaagtctgg cagggcctgg cactgctctc agaagccatc    300

ctgcggggtc aggccctgtt ggccaacgcc tcccagccat ctgagactcc gcagctgcat    360

gtggacaaag ccgtcagcag cctgcgcagc ctcacctctc tgcttcgggc gctgggagcc    420

cagaaggagg ccatgtccct tccagaggaa gcctctcctg ctccactccg aacattcact    480

gttgatactt tgtgcaaact tttccgaatc tactccaatt tcctccgtgg aaagctgaca    540

ctgtacacag gggaggcctg cagaagagga gacaggtga                           579
```

<210> SEQ ID NO 3
<211> LENGTH: 192
<212> TYPE: PRT
<213> ORGANISM: Canis familiaris

<400> SEQUENCE: 3

```
Met Gly Ala Cys Glu Cys Pro Ala Leu Phe Leu Leu Leu Ser Leu Leu
  1               5                  10                  15

Leu Leu Pro Leu Gly Leu Pro Val Leu Gly Ala Pro Pro Arg Leu Ile
             20                  25                  30

Cys Asp Ser Arg Val Leu Glu Arg Tyr Ile Leu Glu Ala Arg Glu Ala
         35                  40                  45

Glu Asn Val Thr Met Gly Cys Ala Gln Gly Cys Ser Phe Ser Glu Asn
     50                  55                  60

Ile Thr Val Pro Asp Thr Lys Val Asn Phe Tyr Thr Trp Lys Arg Met
 65                  70                  75                  80

Asp Val Gly Gln Gln Ala Leu Glu Val Trp Gln Gly Leu Ala Leu Leu
                 85                  90                  95

Ser Glu Ala Ile Leu Arg Gly Gln Ala Leu Leu Ala Asn Ala Ser Gln
```

-continued

```
            100                 105                 110

Pro Ser Glu Thr Pro Gln Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Met Ser Leu Pro Glu Glu Ala Ser Pro Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190


<210> SEQ ID NO 4
<211> LENGTH: 23
<212> TYPE: DNA
<213> ORGANISM: Canis familiaris

<400> SEQUENCE: 4

gttgggcagc aggccttgga agt                                          23


<210> SEQ ID NO 5
<211> LENGTH: 20
<212> TYPE: DNA
<213> ORGANISM: Canis familiaris

<400> SEQUENCE: 5

ctgggctccc agcgcccgaa                                              20
```

What is claimed is:

1. An isolated nucleic acid molecule encoding a canine erythropoietin, wherein the canine erythropoietin has [an] *the* amino acid sequence of SEQ ID NO:3.

2. The nucleic acid molecule of claim 1, wherein the nucleic acid molecule comprises bases 361–4491 of the nucleotide sequence of SEQ ID NO:
1.

3. The nucleic acid molecule of claim 1, wherein the nucleic acid molecule comprises the nucleotide sequence of SEQ ID NO:2.

4. An expression vector comprising the nucleic acid molecule of claim 1, wherein the nucleic acid is foreign to the expression vector.

5. An expression vector according to claim 4, wherein the expression vector is pLEN.

6. An expression vector according to claim 6, wherein the nucleic acid molecule is inserted into the expression vector in proper sense orientation and correct reading frame.

7. A host cell comprising the expression vector of claim 4.

8. The host cell according to claim 7, wherein the host-cell is a mammalian-cell.

9. The host cell according to claim 8, wherein the mammalian host cell is a Chinese hamster ovary cell.

10. A host cell comprising the isolated nucleic acid molecule of claim 1, wherein the nucleic acid molecule is foreign to the host cell.

11. An isolated canine erythropoietin protein or [polypeptided] *polypeptide* having [an] *the* amino acid sequence of SEQ ID NO:3.

12. The protein or polypeptide according to claim 11, wherein the protein or polypeptide is encoded by a nucleic acid molecule comprising bases 361–4491 of the nucleotide of SEQ ID NO:1.

13. The protein or polypeptide according to claim 11, wherein the protein or polypeptide is encoded by a nucleic acid molecule having [an] *the* nucleotide sequence of SEQ ID NO:2.

14. A pharmaceutical composition comprising:

a protein or polypeptide according to claim 11 and a pharmaceutically acceptable diluent, adjuvant, or carrier.

15. A method for providing erythropoietin therapy to a dog comprising:

administering an effective amount of the pharmaceutical composition of claim 14 to the dog.

16. A method for providing erythropoietin therapy to a cat comprising:

administering an effective amount of the pharmaceutical composition of claim 14 to the cat.

* * * * *